US007582296B2

(12) United States Patent
Gilles et al.

(10) Patent No.: US 7,582,296 B2
(45) Date of Patent: Sep. 1, 2009

(54) ANTI-IDIOTYPIC ANTIBODIES AGAINST FACTOR VIII INHIBITOR AND USES THEREOF

(75) Inventors: Jean Guy G. Gilles, Brussels (BE); Jean-Marie R. Saint-Remy, Grez-Doiceau (BE); Marc G. Jacquemin, Sart-Bernard (BE)

(73) Assignee: D. Collen Research Foundation VZW, Leuven (BE)

( * ) Notice: Subject to any disclaimer, the term of this patent is extended or adjusted under 35 U.S.C. 154(b) by 236 days.

(21) Appl. No.: 10/523,444

(22) PCT Filed: Jul. 28, 2003

(86) PCT No.: PCT/EP03/08365

§ 371 (c)(1),
(2), (4) Date: Jan. 31, 2005

(87) PCT Pub. No.: WO2004/014955

PCT Pub. Date: Feb. 19, 2004

(65) Prior Publication Data

US 2006/0239998 A1 Oct. 26, 2006

(30) Foreign Application Priority Data

Jul. 31, 2002 (EP) ................... 02447150

(51) Int. Cl.
*A61K 39/395* (2006.01)
(52) U.S. Cl. .............. 424/131.1; 424/133.1; 424/141.1; 424/145.1; 435/7.1; 435/327; 530/387.2; 530/387.3; 530/388.1; 530/388.25
(58) Field of Classification Search ........................ None
See application file for complete search history.

(56) References Cited

FOREIGN PATENT DOCUMENTS

WO WO 96/27010 A1 * 6/1996
WO WO 99/58680 11/1999
WO WO 01/04269 1/2001

OTHER PUBLICATIONS

Janeway et al., Immunobiology, third edition, Garland Press, 1997, pp. 3:7-3:11,.*
Rudikoff et al. PNAS USA, 1982, 79:1979-1983.*
Gilles et al., Thrombosis and Haemostasis 1997, 78:641-6.*
Shima et al., Thrombosis and Haemostasis, 1993, 69:240-246.*
Muhle et al., Thrombosis and Haemostasis, 2004, 91:619-625.*
Genbank accession No. AAW27416 corresponding to the International Application WO9710354-A1 (Kyowa Hakko Kogyo KK). Mar. 20, 1997.
Genbank accession No. AAR52526 corresponding to the European Application EP592106-A1 (Immunogen Inc.) Apr. 13, 1994.
Genbank accession No. AX417628 corresponding to the International Application WO231510 (PEPSCCAN Systems BV) Jun. 18, 2002.
Genbank accession No. AR144014 corresponding to the U.S. Application US6210671 (Protein Design Labs, Inc.) Apr. 3, 2001.
Genbank accession No. AAT38510 corresponding to the International Application WO9632495-A1 (LG Chem. Ltd.) Apr. 6, 1996.
Gilles et al., "Antibodies to Idiotypes of Human Monoclonal Antifactor VIII (FVIII) Antibodies Neutralise Their Inhibitory Activity," Blood 94 (Suppl. 10, Part 1):460, abstract 2048 (1999).
Gilles et al., "Neutralization Antiidiotypic Antibodies to Factor VIII Inhibitors After Desensitization in Patients with Hemophilia A," J. Clin. Invest. 97:1382-1388 (1996).
Jacquemin, "Mechanism and Kinetics of Factor VIII Inactivation:Study With an IgG4 Monoclonal Antibody Derived from a Hemophilia A Patient With Inhibitor,", Blood 92:496-506 (1998).
Lubahn and Reisner, "Characterizatino of a Monoclonal Anti-Idiotype Antibody to Human Anti-Factor VIII Antibodies," Proc. Natl. Acad. Sci. USA 87:8232-8236 (1990).
Saint-Remy, "Anti-Idiotypic Antibodies: From Regulation to Therapy of Factor VIII Inhibitors," Vox Sang 77 (supp 1):21-24 (1999).
Algiman et al., "Natural antibodies to factor VIII (anti-hemophilic factor) in healthy individuals," *Proceedings of the National Academy of Sciences USA* 89: 3795-3799 (1992).
Gilles et al., "Antibodies of idiotypes of human monoclonal anti-factor VIII (FVIII) antibodies neutralise their inhibitory activity," *Blood*, 94(10 Suppl. 1 Part 1) 460a, Abstract# 2048 (Nov. 15, 1999).
Gilles et al., "Anti-factor VIII Antibodies of Hemophiliac Patients are Frequently Directed Towards Nonfunctional Determinants and Do Not Exhibit Isotypic Restriction," Blood 82(8): 2452-2461 (1993).
Gilles et al., "Healthy Subjects Produce both Anti-Factor VIII and Specific Anti-Idiotypic Antibodies," *Journal of Clinical Investigation* 94(4): 1496-1505 (1994).
Gilles et al., "Neutralizing Antiidiotypic Antibodies to Factor VIII Inhibitors after Desensitization in Patients with Hemophilia A," *Journal of Clinical Investifation* 97(6): 1382-1388 (1996).
Jacquemin et al., "A human antibody directed to the factor VIII C1 domain inhibits factor VIII cofactor activity and binding to von Willebrand factor," *Blood* 95(1): 156-163 (2000).
Jacquemin et al., "Mechanism and Kinetics of Factor VIII Inactivation: Study With an IgG4 Monoclonal Antibody Derived From a Hemophilia A Patient With Inhibitor" *Blood* 92(2): 496-506 (1998).
Kaufman et al., "Synthesis, Processing, and Secretion of Recombinant Human Factor VIII Expressed in Mammalian Cells," *The Journal of Biological Chemistry* 263(13): 6352-6362 (1988).
Lenting et al., "The Light Chain of Factor VIII Comprises a Binding Site for Low Density Lipoprotein Receptor-related Protein," *The Journal of Biological Chemistry* 274(34): 23734-23739 (1999).

(Continued)

*Primary Examiner*—Michael Szperka
(74) *Attorney, Agent, or Firm*—Clark & Elbing LLP

(57) ABSTRACT

The present invention discloses anti-idiotypic antibodies and fragments thereof against inhibitory Factor VIII anti-bodies, said inhibitory antibodies having an affinity for the C2 domain of Factor VIII. The anti-idiotypic antibodies of the present invention are able to completely neutralise in vitro and in an in vivo mouse model the inhibitory activity of FVIII inhibitors. The anti idiotypic antibodies of the present invention can be applied for the prevention, treatment or reduction of bleeding disorders of hemophilia patients with inhibitory antibody against the C2 domain of Factor VIII.

20 Claims, 10 Drawing Sheets

OTHER PUBLICATIONS

Figure 1:
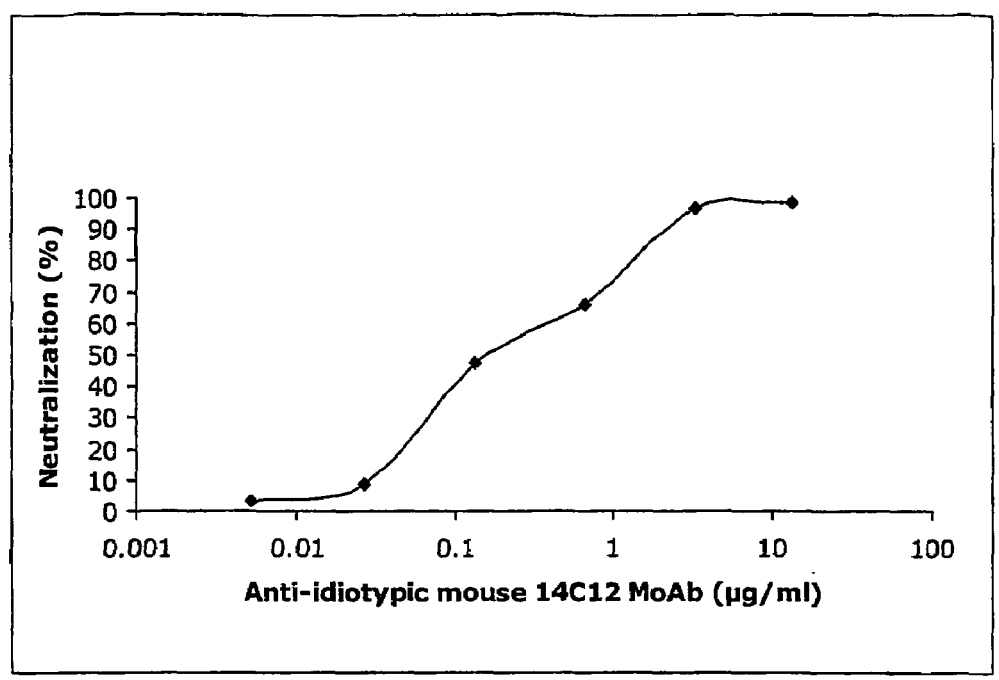

Lubahn et al., "Characterization of a monoclonal anti-idiotype antibody to human anti-factor VIII antibodies," *Proceedings of the National Academy of Sciences USA* 87: 8232-8236 (1990).

Manivel et al., "Maturation of an Antibody Reponse Is Governed by Modulations in Flexibility of the Antigen-Combining Site," *Immunity* 13: 611-620 (2000).

Pratt et al., "Structure of the C2 domain of human factor VIII at 1.5 Å resolution," *Nature* 402: 439-442 (1999).

Saenko et al., "Role of the Low Density Lipoprotein-related Protein Receptor in Mediation of Factor VIII Catabolism," *The Journal of Biological Chemistry* 274(53): 37685-37692 (1999).

Saint-Remy et al., "Anti-Idiotypic antibodies: From Regulation to Therapy of Factor VIII Inhibitors," *Vox Sanguinis*, S. Karger AG, Basel, CH, 77(Suppl. 1): 21-24 (1999).

Singh et al., "Antithrombotic effects of controlled inhibition of factor VIII with a partially inhibitory human monoclonal antibody in a murine vena cava thrombosis model," *Blood* 99(9): 3235-3240 (2002).

Spiegel Jr. et al., "Structure of a factor VIII C2 domain-immunoglobulin G4κ Fab complex: identification of an inhibitory antibody epitope on the surface of factor VIII," *Blood* 98(1): 13-19 (2001).

Van den Brink et al., "Two classes of germline genes both derived from the $V_H1$ family direct the formation of human antibodies that recognize distinct antigenic sites in the C2 domain of factor VIII," *Blood* 99(8): 2828-2834 (2002).

Wilbur et al., "Rapid similarity searches of nucleic acid and protein data banks," *Proceedings of the National Academy of Sciences USA* 80: 726-730 (1983).

International Search Report issued in PCT/EP03/08365 (dated Dec. 4, 2003).

International Preliminary Examination Report issued in PCT/EP03/08365 (dated Aug. 17, 2004).

International Preliminary Examination Report issued in PCT/EP03/08365 (dated Sep. 21, 2004).

Genebank accession No. AAW27416 corresponding to the international application WO9710354 (Kyowa Hakko Kogyo KK). Mar. 20, 1997.

Genebank accession No. AAR52526 corresponding to the European application EP592106 (Immunogen Inc.) Apr. 13, 1994.

Genebank accession No. AX417628 corresponding to the international application No. WO231510 (PEPSCAN Systems BV) (NL) Jun. 18, 2002.

Genebank accession No. AR144014 corresponding to the U.S. patent US6210671-A/3 (Protein Design Labs, Inc.) Apr. 3, 2001.

Genebank accession No. AAT38510 corresponding to the international application WO9632495-A/1 (LG Chem Ltd.) Apr. 6, 1996.

Jacquemin et al. "Mechanism and Kinetics of Factor VIII Inactivation: Study with an IgG4 Monoclonal Antibody Derived From a Hemophilia A Patient With Inhibitor," Blood 92(2):496-506 (1998).

Sultan et al., "Recovery from anti-VIII:C (antihemophilic factor) autoimmune disease is dependent on generation of antiidiotypes against anti-VIII:C autoantibodies," Proc. Natl. Acad. Sci. USA 84:828-831 (1987).

EPO Communication pursuant to Article 96(2) EPC (EP Application No. 03 784 106.1-1222), dated Oct. 10, 2006.

Office Action for Canadian Patent Application No. 2,494,698, dated May 22, 2009.

* cited by examiner

```
GAG GTC CAG CTT CAG CAG TCT GGA CCT GAG CTG GTT AAG CCT GGG GCT TCA GTG AAG CTG
                                                                                  60
 E   V   Q   L   Q   Q   S   G   P   E   L   V   K   P   G   A   S   V   K   L
20

TCC TGC AAG GCT TCT GGA TAC ACA TTC ACT AGC TCT GTT ATG CAC TGG CTG AAG CAG AAG
                                                                                  120
 S   C   K   A   S   G   Y   T   F   T   S   S   V   M   H   W   L   K   Q   K
40
                 -----------CDR1 (G26-L37)-----------------------

TCT GGG CAG GGC CTT GAG TGG ATT GGA TAT ATT AAT CCT TAC AAT GAT GGT ACT AAG TAC
                                                                                  180
 S   G   Q   G   L   E   W   I   G   Y   I   N   P   Y   N   D   G   T   K   Y
60
                             ---------------------CDR2 (G50-A66)----------

AAT GAG AAG TTC ACA GCC AAG GCC ACA CTG ACT TCA GAC AAA TCC TCC AGC ACA GTC TAC
                                                                                  240
 N   E   K   F   T   A   K   A   T   L   T   S   D   K   S   S   S   T   V   Y
80
-----------------------

ATG GAG CTC AGC GGC CTG ACC TCT GAG GAC TTT GCG GTC TAT TAC TGT GCA CGA TCG GGA
                                                                                  300
 M   E   L   S   G   L   T   S   E   D   F   A   V   Y   Y   C   A   R   S   G
100
                                                                          ------

GGT TTA CTA CGA GGT TAC TGG TAC TTC GAT GTC TGG GGC GCA GGG ACC ACG GTC ACC GTC
                                                                                  360
 G   L   L   R   G   Y   W   Y   F   D   V   W   G   A   G   T   T   V   T   V
120
CDR3 (S99-V111)---------------------------

TCC TCA GCC AAA ACA ACA GCC CCA TCG GTC TAT CCC TTG GTC CCT GGC TGC
              411
 S   S   A   K   T   T   A   P   S   V   Y   P   L   V   P   G   C
              137
```

Figure 3a

>14C12A1LC

```
GAT CTT GTG CTA ACT CAG TCT CCA GCC ACC CTG TCT GTG ACT CCA GGA GAT AGT GTC AGT
60
 D   L   V   L   T   Q   S   P   A   T   L   S   V   T   P   G   D   S   V   S
20

CTT TCC TGT AGG GCC AGC CAA GAT ATT ACC AAC ACC CTT CAC TGG TAT CAT CAA AAA TCA
120
 L   S   C   R   A   S   Q   D   I   T   N   T   L   H   W   Y   H   Q   K   S
40
                 -----------CDR1 (R24-H34)------------------

CAT GAG TCT CCA AGG CTT CTC ATC AAG TAT GTT TCC CAG TCC ATC TCT GGG ATC CCC TCC
180
 H   E   S   P   R   L   L   I   K   Y   V   S   Q   S   I   S   G   I   P   S
60
                                     ------CDR2 (Y50-S56)------

AGG TTC AGT GGC AGT GGA TCA GGG ACA GTT TTC ACT CTC AGT ATC AAC AGT GTG GAG ACT
240
 R   F   S   G   S   G   S   G   T   V   F   T   L   S   I   N   S   V   E   T
80

GAA GAT TTT GGA GTG TAT TTC TGT CAG CAG AGT ACC AGC TGG CCG TAC ACA TTC GGA GGG
300
 E   D   F   G   V   Y   F   C   Q   Q   S   T   S   W   P   Y   T   F   G   G
100
                             -------------CDR3 (Q89-T97)-------

GGG ACC AAG TTG GAA ATA AAA CGG GCT GAT GCT GCA CCA ACT GTA TCC ATC TTC CCA CCA
360
 G   T   K   L   E   I   K   R   A   D   A   A   P   T   V   S   I   F   P   P
120

TCC AGT gAG
369
 S   S   E
        123
```

Figure 3b

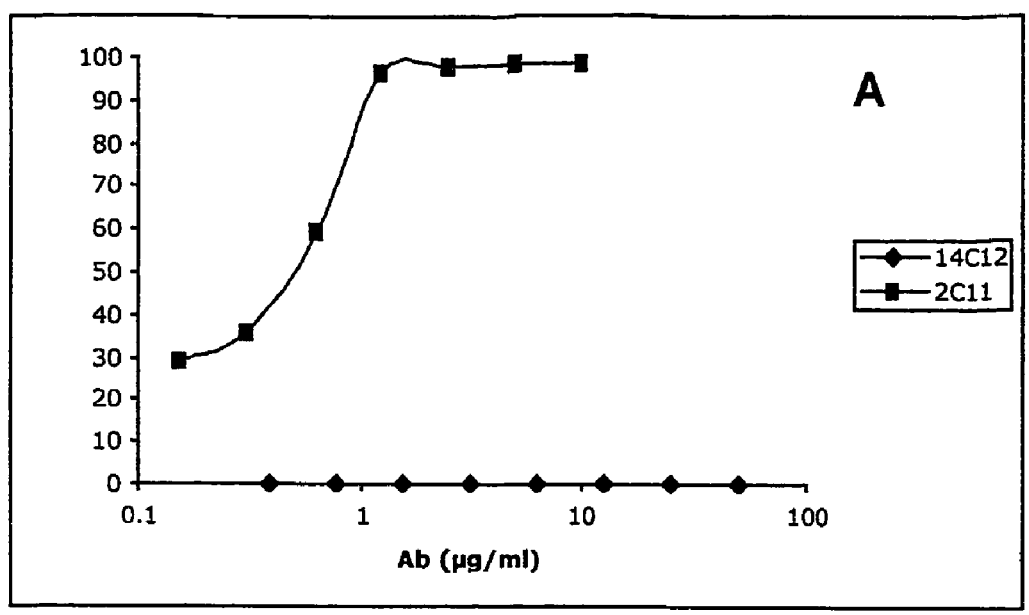
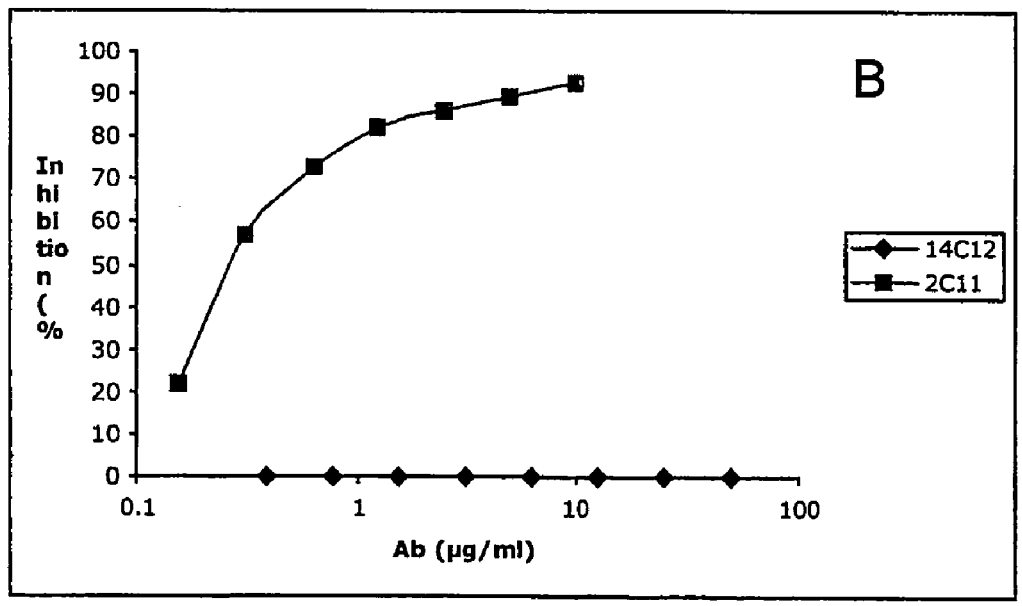
Figure 7

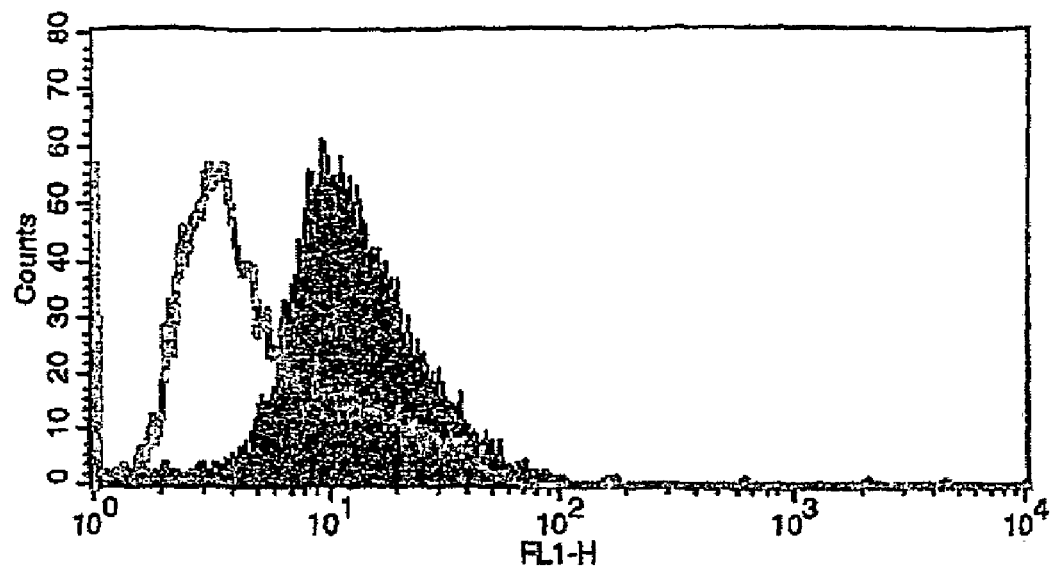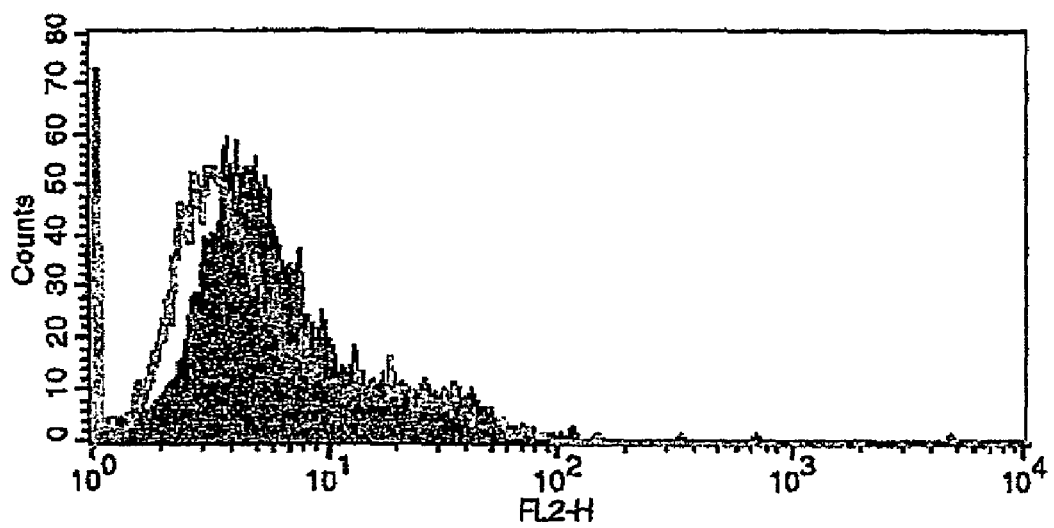
Figure 9

SEQUENCE LISTING

```
<160> NUMBER OF SEQ ID NOS: 10

<210> SEQ ID NO 1
<211> LENGTH: 411
<212> TYPE: DNA
<213> ORGANISM: Mus musculus
<220> FEATURE:
<221> NAME/KEY: CDS
<222> LOCATION: (1)...(411)
<220> FEATURE:
<221> NAME/KEY: V_region
<222> LOCATION: (1)...(411)
<223> OTHER INFORMATION: 14C12 monoclonal antibody heavy chain
<220> FEATURE:
<221> NAME/KEY: misc_feature
<222> LOCATION: (78)...(111)
<223> OTHER INFORMATION: CDR1
<220> FEATURE:
<221> NAME/KEY: misc_feature
<222> LOCATION: (150)...(198)
```

<223> OTHER INFORMATION: CDR2
<220> FEATURE:
<221> NAME/KEY: misc_feature
<222> LOCATION: (297)...(333)
<223> OTHER INFORMATION: CDR2

<400> SEQUENCE: 1

| | | | | | | | | | | | | | | | | |
|---|---|---|---|---|---|---|---|---|---|---|---|---|---|---|---|---|
| gag | gtc | cag | ctt | cag | cag | tct | gga | cct | gag | ctg | gtt | aag | cct | ggg | gct | 48 |
| Glu | Val | Gln | Leu | Gln | Gln | Ser | Gly | Pro | Glu | Leu | Val | Lys | Pro | Gly | Ala | |
| 1 | | | | 5 | | | | | 10 | | | | | 15 | | |
| tca | gtg | aag | ctg | tcc | tgc | aag | gct | tct | gga | tac | aca | ttc | act | agc | tct | 96 |
| Ser | Val | Lys | Leu | Ser | Cys | Lys | Ala | Ser | Gly | Tyr | Thr | Phe | Thr | Ser | Ser | |
| | | | 20 | | | | | 25 | | | | | 30 | | | |
| gtt | atg | cac | tgg | ctg | aag | cag | aag | tct | ggc | cag | ggc | ctt | gag | tgg | att | 144 |
| Val | Met | His | Trp | Leu | Lys | Gln | Lys | Ser | Gly | Gln | Gly | Leu | Glu | Trp | Ile | |
| | | 35 | | | | | 40 | | | | | 45 | | | | |
| gga | tat | att | aat | cct | tac | aat | gat | ggt | act | aag | tac | aat | gag | aag | ttc | 192 |
| Gly | Tyr | Ile | Asn | Pro | Tyr | Asn | Asp | Gly | Thr | Lys | Tyr | Asn | Glu | Lys | Phe | |
| 50 | | | | | 55 | | | | | 60 | | | | | | |
| aca | gcc | aag | gcc | aca | ctg | act | tca | gac | aaa | tcc | tcc | agc | aca | gtc | tac | 240 |
| Thr | Ala | Lys | Ala | Thr | Leu | Thr | Ser | Asp | Lys | Ser | Ser | Ser | Thr | Val | Tyr | |
| 65 | | | | 70 | | | | | 75 | | | | | 80 | | |
| atg | gag | ctc | agc | ggc | ctg | acc | tct | gag | gac | ttt | gcg | gtc | tat | tac | tgt | 288 |
| Met | Glu | Leu | Ser | Gly | Leu | Thr | Ser | Glu | Asp | Phe | Ala | Val | Tyr | Tyr | Cys | |
| | | | 85 | | | | | 90 | | | | | 95 | | | |
| gca | cga | tcg | gga | ggt | tta | cta | cga | ggt | tac | tgg | tac | ttc | gat | gtc | tgg | 336 |
| Ala | Arg | Ser | Gly | Gly | Leu | Leu | Arg | Gly | Tyr | Trp | Tyr | Phe | Asp | Val | Trp | |
| | | | 100 | | | | | 105 | | | | | 110 | | | |
| ggc | gca | ggg | acc | acg | gtc | acc | gtc | tcc | tca | gcc | aaa | aca | aca | gcc | cca | 384 |
| Gly | Ala | Gly | Thr | Thr | Val | Thr | Val | Ser | Ser | Ala | Lys | Thr | Thr | Ala | Pro | |
| | | 115 | | | | | 120 | | | | | 125 | | | | |
| tcg | gtc | tat | ccc | ttg | gtc | cct | ggc | tgc | | | | | | | | 411 |
| Ser | Val | Tyr | Pro | Leu | Val | Pro | Gly | Cys | | | | | | | | |
| | 130 | | | | | 135 | | | | | | | | | | |

<210> SEQ ID NO 2
<211> LENGTH: 137
<212> TYPE: PRT
<213> ORGANISM: Mus musculus

<400> SEQUENCE: 2

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Val Met His Trp Leu Lys Gln Lys Ser Gly Gln Gly Leu Glu Trp Ile
        35                  40                  45

Gly Tyr Ile Asn Pro Tyr Asn Asp Gly Thr Lys Tyr Asn Glu Lys Phe
50                  55                  60

Thr Ala Lys Ala Thr Leu Thr Ser Asp Lys Ser Ser Ser Thr Val Tyr
65                  70                  75                  80

Met Glu Leu Ser Gly Leu Thr Ser Glu Asp Phe Ala Val Tyr Tyr Cys
                85                  90                  95

Ala Arg Ser Gly Gly Leu Leu Arg Gly Tyr Trp Tyr Phe Asp Val Trp
            100                 105                 110

Gly Ala Gly Thr Thr Val Thr Val Ser Ser Ala Lys Thr Thr Ala Pro
        115                 120                 125

Ser Val Tyr Pro Leu Val Pro Gly Cys
    130                 135

<210> SEQ ID NO 3
<211> LENGTH: 369
<212> TYPE: DNA
<213> ORGANISM: Mus musculus
<220> FEATURE:
<221> NAME/KEY: CDS
<222> LOCATION: (1)...(369)
<220> FEATURE:
<221> NAME/KEY: V_region
<222> LOCATION: (1)...(369)
<223> OTHER INFORMATION: 14C12 monoclonal antibody light chain
<220> FEATURE:
<221> NAME/KEY: misc_feature
<222> LOCATION: (72)...(102)
<223> OTHER INFORMATION: CDR1
<220> FEATURE:
<221> NAME/KEY: misc_feature
<222> LOCATION: (150)...(168)
<223> OTHER INFORMATION: CDR2
<220> FEATURE:
<221> NAME/KEY: misc_feature
<222> LOCATION: (267)...(291)
<223> OTHER INFORMATION: CDR3

<400> SEQUENCE: 3

```
gat ctt gtg cta act cag tct cca gcc acc ctg tct gtg act cca gga      48
Asp Leu Val Leu Thr Gln Ser Pro Ala Thr Leu Ser Val Thr Pro Gly
 1               5                  10                  15 gat agt gtc agt ctt tcc tgt agg gcc agc caa gat att acc aac acc      96
Asp Ser Val Ser Leu Ser Cys Arg Ala Ser Gln Asp Ile Thr Asn Thr
             20                  25                  30 ctt cac tgg tat cat caa aaa tca cat gag tct cca agg ctt ctc atc    144
Leu His Trp Tyr His Gln Lys Ser His Glu Ser Pro Arg Leu Leu Ile
         35                  40                  45 aag tat gtt tcc cag tcc atc tct ggg atc ccc tcc agg ttc agt ggc    192
Lys Tyr Val Ser Gln Ser Ile Ser Gly Ile Pro Ser Arg Phe Ser Gly
     50                  55                  60 agt gga tca ggg aca gtt ttc act ctc agt atc aac agt gtg gag act    240
Ser Gly Ser Gly Thr Val Phe Thr Leu Ser Ile Asn Ser Val Glu Thr
 65                  70                  75                  80 gaa gat ttt gga gtg tat ttc tgt cag cag agt acc agc tgg ccg tac    288
Glu Asp Phe Gly Val Tyr Phe Cys Gln Gln Ser Thr Ser Trp Pro Tyr
                 85                  90                  95 aca ttc gga ggg ggg acc aag ttg gaa ata aaa cgg gct gat gct gca    336
Thr Phe Gly Gly Gly Thr Lys Leu Glu Ile Lys Arg Ala Asp Ala Ala
            100                 105                 110 cca act gta tcc atc ttc cca cca tcc agt gag                        369
Pro Thr Val Ser Ile Phe Pro Pro Ser Ser Glu
        115                 120
```

<210> SEQ ID NO 4
<211> LENGTH: 123
<212> TYPE: PRT
<213> ORGANISM: Mus musculus

<400> SEQUENCE: 4

```
Asp Leu Val Leu Thr Gln Ser Pro Ala Thr Leu Ser Val Thr Pro Gly
 1               5                  10                  15

Asp Ser Val Ser Leu Ser Cys Arg Ala Ser Gln Asp Ile Thr Asn Thr
             20                  25                  30

Leu His Trp Tyr His Gln Lys Ser His Glu Ser Pro Arg Leu Leu Ile
         35                  40                  45

Lys Tyr Val Ser Gln Ser Ile Ser Gly Ile Pro Ser Arg Phe Ser Gly
     50                  55                  60
```

```
Ser Gly Ser Gly Thr Val Phe Thr Leu Ser Ile Asn Ser Val Glu Thr
 65                  70                  75                  80

Glu Asp Phe Gly Val Tyr Phe Cys Gln Gln Ser Thr Ser Trp Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu
            115                 120

<210> SEQ ID NO 5
<211> LENGTH: 12
<212> TYPE: PRT
<213> ORGANISM: Mus musculus

<400> SEQUENCE: 5

Gly Tyr Thr Phe Thr Ser Ser Val Met His Trp Leu
 1               5                  10

<210> SEQ ID NO 6
<211> LENGTH: 18
<212> TYPE: PRT
<213> ORGANISM: Mus musculus

<400> SEQUENCE: 6

Gly Tyr Ile Asn Pro Tyr Asn Asp Gly Thr Lys Tyr Asn Glu Lys Phe
 1               5                  10                  15

Thr Ala

<210> SEQ ID NO 7
<211> LENGTH: 13
<212> TYPE: PRT
<213> ORGANISM: Mus musculus

<400> SEQUENCE: 7

Ser Gly Gly Leu Leu Arg Gly Tyr Trp Tyr Phe Asp Val
 1               5                  10

<210> SEQ ID NO 8
<211> LENGTH: 11
<212> TYPE: PRT
<213> ORGANISM: Mus musculus

<400> SEQUENCE: 8

Arg Ala Ser Gln Asp Ile Thr Asn Thr Leu His
 1               5                  10

<210> SEQ ID NO 9
<211> LENGTH: 7
<212> TYPE: PRT
<213> ORGANISM: Mus musculus

<400> SEQUENCE: 9

Tyr Val Ser Gln Ser Ile Ser
 1               5

<210> SEQ ID NO 10
<211> LENGTH: 9
```

```
-continued

<212> TYPE: PRT
<213> ORGANISM: Mus musculus

<400> SEQUENCE: 10

Gln Gln Ser Thr Ser Trp Pro Tyr Thr
 1               5
```

ANTI-IDIOTYPIC ANTIBODIES AGAINST FACTOR VIII INHIBITOR AND USES THEREOF

CROSS REFERENCE TO RELATED APPLICATIONS

This application is the U.S. national stage of international application PCT/EP03/008365, filed Jul. 28, 2003, which claims benefit of EP application 02447150.0, filed Jul. 31, 2002.

FIELD OF THE INVENTION

The present invention relates to pharmaceutical compositions for the treatment of haemophilia, especially for the treatment of human patients who have developed FVIII inhibitors directed to the C2 domain. The present invention provides anti-idiotypic antibodies against FVIII inhibitors directed to the C2 domain. The invention further relates to monoclonal cell lines expressing such anti-idiotypic antibodies. The invention also relates to pharmaceutical compositions comprising the anti-idiotypic antibodies of the present invention.

BACKGROUND OF THE INVENTION

Haemophilia A is an X-linked disorder characterised by the absence or insufficient amount of functional factor VIII, a 330 kD glycoprotein molecule produced by the liver as a single polypeptide chain of 2332 amino acids. This deficiency affects 1 in 10,000 males and can result in uncontrolled bleeding in joints, muscles and soft tissues. Patients affected by the severe form of the disease (FVIII activity lower than 1% of normal level) suffer from spontaneous bleedings. Patients with corresponding FVIII activity from 1 to 5%, or higher than 5% are defined as moderate or mild haemophilia A, respectively, and suffer from limited bleeding occurring after minor trauma or surgery. The coagulation pathway can be restored by administration of FVIII concentrates prepared from plasma or produced by recombinant cDNA technology.

The human FVIII gene has been isolated and expressed in mammalian cells, as reported by various authors, including Wood et al. in *Nature* (1984) 312: 330-337 and the amino-acid sequence was deduced from cDNA. U.S. Pat. No. 4,965, 199 discloses a recombinant DNA method for producing FVIII in mammalian host cells and purification of human FVIII. The human FVIII detailed structure has been extensively investigated. The cDNA nucleotide sequence encoding human FVIII and predicted amino-acid sequence have been disclosed for instance in U.S. Pat. No. 5,663,060. In a FVIII molecule, a domain may be defined as a continuous sequence of amino-acids that is defined by internal amino-acid sequence homology and sites of proteolytic cleavage by a suitable protease such as thrombin. The FVIII proteins has been described to consist of different domains, which for the human amino-acid sequence correspond to: A1, residues 1-372; A2, residues 373-740; B, residues 741-1648; A3, residues 1690-2019; C1, residues 2020-2172; C2, residues 2173-2332. The remaining sequence, residues 1649-1689, is usually referred to as the FVIII light chain activation peptide. FVIII is produced as a single polypeptide chain which, upon processing within the cell, is rapidly cleaved after secretion to form a heterodimer made of a heavy chain containing the A1, A2 and B domains and a light chain made of the A3-C1-C2 domains, according to Kaufman et al. (1988, *J Biol Chem* 263:6352-6362). The two chains are non-covalently bound by divalent cations. Both the single-chain polypeptide and the heterodimer circulate in plasma as inactive precursors, as taught by Ganz et al. (1988, *Eur J Biochem* 170:521-528). Activation of factor VIII in plasma initiates by thrombin cleavage between the A2 and B domains, which releases the B domain and results in a heavy chain consisting of the A1 and A2 domains, according to Eaton et al. (1986, *Biochemistry* 25:505-512). Human recombinant FVIII may be produced by genetic recombination in mammalian cells such as CHO (Chinese Hamster Ovary) cells, BHK (Baby Hamster Kidney) cells or other equivalent cells.

Pratt et al. (1999, *Nature* 402:439-42) disclose the detailed structure of the carboxy-terminal C2 domain of human FVIII, which contains sites that are essential for its binding to von Willebrand factor (vWF) and to negatively charged phospholipid surfaces. This structure, which reveals a beta-sandwich core from which two beta-turns and a loop display a group of solvent-exposed hydrophobic residues, partly explains mutations in the C2 region that lead to bleeding disorders in haemophilia A. According to Gale et al. (2000, *Thromb. Haemost* 83:78-85), of the at least 250 missense mutations that cause FVIII deficiency and haemophilia A, 34 are in the C domains.

FVIII is a cofactor of the intrinsic pathway of the coagulation cascade, which acts by increasing the proteolytic activity of activated factor IX over factor X, in the so-called tenase complex formation. Patients suffering from haemophilia A present bleedings which are either spontaneous in the severe form of the disease, or occur after trauma in the mild/moderate forms.

Haemophilia A patients are usually treated by replacement therapy, which consists in infusing human FVIII either purified from pools of donor plasma, or obtained by cDNA recombination technology.

The majority of the patients are immunologically unresponsive to these infusions, but for yet unclear reasons, 25% of them mount an IgG immune response towards FVIII, which can result in complete inhibition of the procoagulant activity of infused FVIII (Briët E et al. in (1994) *Throm. Haemost.;* 72: 162-164; Ehrenforth S et al. in (1992) *Lancet,* 339:594). Such specific IgG, which belong to the IgG 1, 2, 4 subclasses, are called FVIII inhibitors. Published studies have demonstrated that the anti-FVIII immune response is polyclonal, and primarily directed towards the A2, A3 and C2 domains (Scandella D et al. in (1989) *Blood;* 74: 1618-1626; Gilles J G et al. in (1993) *Blood;* 82: 2452-2461).

Recent studies using human monoclonal antibodies derived from the peripheral memory B cell repertoire of inhibitor patients indicated that important epitopes are also located on the C1 domain (Jacquemin M et al. in (2000) *Blood* 95:156-163). The mechanism by which anti-FVIII antibodies interfere with the function of FVIII are numerous, including proteolytic cleavage of FVIII and interaction with different partners such as von Willebrand factor (vWF), phospholipids (PL), FIX, FXa or APC. Most of these mechanisms are now well described in studies using mouse or human anti-FVIII antibodies. Thus, antibodies can reduce the rate at which FVIII is activated by either binding to a proteolytic cleavage site or by inducing a 3D conformational change in FVIII that renders it less amenable to proteolysis. Antibodies interfering with the binding of vWF to FVIII appear to be very efficient as inhibitors, as shown in recent studies using human monoclonal antibodies directed towards the C2 domain, which is one of the major vWF binding sites (Jacquemin M et al in (1998) *Blood;* 92:496-501). Suppressing the production of inhibitors and establishing a state of immune unresponsiveness to FVIII remains a major goal. The medical community is, however, far from reaching these goals, due basically to the limited understanding of the mechanisms underlying specific antibody production and regulation.

Presently, to control such an immune response, several treatments are used including bypassing agents such as desmopressin (DDAVP), agents promoting coagulation such as prothrombin complex concentrates (PCC) or activated PCC, recombinant FVIIa, plasmapheresis and infusions of large or intermediate doses of FVIII (200-300 IU/kg body weight or 25-50 IU/kg body weight, respectively). However, none of these methods are satisfactory and they are all very costly.

Based on these observations and on the understanding of the mechanisms of immune tolerance, anti-idiotypic antibodies appear to be a promising way of treating inhibitors. In fact, it is well established that tolerance to self-protein is first induced at an early stage by clonal deletion of self-reactive B and T cells in the bone marrow and the thymus, respectively. However, not all self-reactive lymphocytes are eliminated by central deletion. Auto-reactive B cells are a common feature of peripheral blood, as well as low- or intermediate-affinity self-reactive T cells. A number of mechanisms by which such auto-reactive cells are rendered non-functioning or are deleted in the periphery have been described. Anti-idiotypic antibodies can represent a third level of tolerance maintenance in this general scheme, with their capacity to fine tune the function of antibodies and maintain a subtle equilibrium between complementary idiotypes expressed on B and T cells.

A good indication of how anti-idiotypic antibodies can exert a regulatory mechanism in the periphery is provided by the demonstration that healthy individuals with normal levels of FVIII produce significant titres of inhibitory antibodies to FVIII (Algiman M et al. in (1992) *Proc Natl Acad Sci USA* 89:3795-3799; Gilles J G et al in (1994) *J Clin Invest* 94:1496-505), the activity of which is undetectable in plasma because of the presence of complementary anti-idiotypic antibodies. However, such a FVIII inhibitory activity can be readily detected when anti-FVIII antibodies are purified by a combination of chromatography and specific immunoadsorption over insolubilized FVIII. The FVIII inhibitory capacity of affinity-purified antibodies was demonstrated to be equal to that of anti-FVIII antibodies purified from haemophilia A patient's plasma with high level of inhibitors, as measured by Bethesda assay (Gilles J G et al. in (1994) *J Clin Invest* 94:1496-505).

Such neutralising anti-idiotypic activity has also been detected in a group of patients successfully desensitised by administration of high doses of FVIII (Gilles J G et al. in (1996) *J Clin Invest* 97:1382-1388). The study demonstrated that the concentration of anti-FVIII antibodies, purified by the same procedure as for healthy donors, did not change during desensitisation and that antibodies maintained their capacity to inhibit the procoagulant function of FVIII, even though the titration of inhibitor using the Bethesda assay in plasma was reduced to undetectable levels. This pointed to the potentially important function of anti-idiotypic regulation in tolerance to FVIII molecule. Therefore, any novel therapy inducing an increased production of anti-idiotypic antibodies can be of interest in the treatment of patients with FVIII-inhibitors. A first approach along these lines has been reported, in which patients were treated with injections of immune complexes made of FVIII and autologous specific antibodies towards FVIII, which resulted in a significant reduction in the level of circulating FVIII inhibitors, which were neutralised by corresponding anti-idiotypic antibodies (Gilles J G, Arnout J. XXI International Congress of the World Federation of Haemophilia 1994 April; abstract). Such an approach can open the way towards new therapeutic strategies, which target FVIII inhibitors at potentially low cost compared to presently available treatments.

Previous findings from the inventors' laboratory have shown that anti-idiotypic antibodies exert physiological properties in the homeostasis of the anti-FVIII immune response. Thus, the peripheral blood of healthy individuals contains antibodies specific for FVIII; some of which have the property of inhibiting the procoagulant function of FVIII (Gilles JGG & Saint-Remy JMR in (1994) J Clin Invest 94: 1496-1505). In these individuals, the function of FVIII is actually not altered, as antibody-mediated FVIII inhibition is neutralised by specific anti-idiotypic antibodies. We therefore concluded that anti-idiotypic antibodies have a physiological relevance in the maintenance of normal FVIII activity.

Moreover, the inventors have shown that when haemophilia A patients with inhibitor are treated by regular infusion of high doses of FVIII, a treatment also called desensitisation or tolerance induction (see above), one of the biological consequences of such infusions is the elicitation of specific anti-idiotypic antibodies able to neutralise the inhibitor (Gilles J G et al. in (1996) *J Clin Invest* 97: 1382-1388). These findings suggest that the use of anti-idiotypic antibodies could represent a valuable approach for the control of FVIII inhibitory antibodies.

The human monoclonal antibody BO2C11 is a FVIII-specific IgG4kappa antibody derived from the natural repertoire of a patient with inhibitor (Jacquemin M G, et al. in (1998) *Blood* 92: 496-506). Ab BO2C11 recognises the C2 domain and inhibits the binding of FVIII to both vWF and phospholipids (PL). This antibody is representative of a major class of human inhibitory antibodies. Its mechanism of action is commonly encountered in patients with inhibitor and C2-specific antibodies are the most frequently observed inhibitory antibodies. Moreover, the exact binding site of Ab BO2C11 on the C2 domain has been deciphered through X-ray analysis of crystals made of the antibody Fab fragments and the C2 domain (Spiegel P. C. Jr. et al. (2001) *Blood* 98: 13-19).

Previous reports have described anti-idiotypic antibodies directed towards anti-FVIII antibodies. Lubahn and Reisner (1990, *Proc Natl Acad Sci. USA* 87: 8232-8236) partially purified human anti-FVIII antibodies by salt precipitation and chromatography from the plasma of a haemophilia A patient with inhibitor. These authors demonstrated that the purified IgG recognised the native FVIII heavy chain and its thrombin-digested 43 kDa chain. The preparation (SP8.4) was injected in mice in an attempt to obtain anti-idiotypic antibodies. Several clones were obtained, with one of them, Mab20-2H, inhibiting the anti-FVIII antibody binding to the heavy chain. In a functional assay, Mab20-2H did not modify the inhibitory activity of SP8.4 IgG fraction, even when added at high concentrations. Mab20-2H detected antibodies in 3.2% of the haemophilic inhibitor plasmas tested, but never neutralised the inhibitory activity. The authors concluded that Mab20-2H recognised a non-inhibitory anti-FVIII antibody that is directed toward the 43 kDa chain (A2 domain) of the FVIII molecule.

Another anti-idiotypic antibody (B6A2C1) was developed and described from the inventors' laboratory (Gilles J G et al in (1999) *Blood* 94, abstract 2048: 460a). This anti-idiotypic antibody is directed towards an anti-FVIII C1 domain inhibitor.

SUMMARY OF THE INVENTION

It is an object of the present invention to provide a pharmaceutical composition for use on human patients suffering from (primary or acquired) haemophilia, who have developed inhibitors against FVIII.

It is a further object of the present invention to provide cell lines for generating neutralising antibodies directed against human FVIII inhibitors as well as the neutralising antibodies.

In a first aspect of the present invention monoclonal anti-idiotypic antibodies against a human Factor VIII inhibitory antibody, which inhibitory antibody is directed towards the C2 domain of Factor VIII, are provided. Anti-idiotypic antibodies of the present invention are further characterised in having the capacity to neutralise by at least 50%, preferably by at least 60%, more preferably by at least 70, even more preferably by at least 80% and most preferably by at least 90%, the inhibition of FVIII procoagulant activity mediated by inhibitory antibodies against the C2 domain of FVIII.

In a further aspect of the present invention, the anti-idiotypic antibody is directed against a FVIII inhibitory antibody of which the heavy chain is encoded by a VH germline segment DP-5 derived from the VH1 family. In yet another aspect of the present invention the Factor VIII inhibitory antibody is Ab BO2C11.

The present invention also relates to humanised anti-idiotypic antibodies.

The present invention also relates to monoclonal anti-idiotypic antibodies, such as the one obtainable from cell line 14C12. The cell line 14C12 was deposited on Jul. 30, 2002 at the Belgian Coordinated Collections of Micro-organisms (BCCM), LMBP (plasmid collection, Laboratorium voor Moleculaire Biologie, Universiteit, K. L. Ledeganckstraat 35, 9000 Gent, Belgium) with Accession Number LMBP 5878CB.

The present invention further relates to anti-idiotypic antibodies wherein the variable heavy chain of anti-idiotypic antibody is encoded by the nucleotide sequence depicted in SEQ ID NO 1 or a nucleotide sequence having at least 70% sequence identity, preferably having at least 80% sequence identity, more preferably having at least 90% sequence identity, even more preferably having at least 95-99% sequence identity with SEQ ID NO 1, and/or wherein the variable light chain of the anti-idiotypic antibody is encoded by the nucleotide sequence depicted in SEQ ID NO 3 or a nucleotide sequence having at least 70% sequence identity, preferably having at least 80% sequence identity, more preferably having at least 90% sequence identity, even more preferably having at least 95-99% sequence identity with SEQ ID NO 3. In particular, the nucleotide sequences may include those which use equivalent trinucleotides to those specified in the SEQ ID No 1 and SEQ ID NO: 3 as determined by the redundancy of the genetic code, thereby preferably retaining the ability to neutralise inhibitory FVIII antibodies.

The present invention further relates to anti-idiotypic antibodies having a variable heavy chain protein sequence as depicted in SEQ ID NO 2 or a protein sequence having at least 70% sequence identity, more preferably at least 80% sequence identity, even more preferably having at least 90% sequence identity, still even more preferably having at least 95% sequence identity, most preferably having at least 99% sequence identity with SEQ ID NO 2 and/or having a variable light chain protein sequence as depicted in SEQ ID NO 4 or a protein sequence having at least 70% sequence identity, more preferably at least 80% sequence identity, even more preferably having at least 90% sequence identity, still even more preferably having at least 95% sequence identity, most preferably having at least 99% sequence identity with SEQ ID NO 4, thereby preferably retaining the ability to neutralise inhibitory FVIII antibodies.

The present invention also relates to anti-idiotypic antibodies wherein the complementarity determining regions (CDR) of the variable heavy and/or light chains of said antibody have at least 70% sequence identity, more preferably have at least 80% sequence identity, even more preferably have at least 90% sequence identity, and most preferably have at least 95-99% sequence identity with the corresponding amino acid sequences depicted in SEQ ID NO 5, SEQ ID NO 6, SEQ ID NO 7, SEQ ID NO 8, SEQ ID NO 9 and SEQ ID NO 10 or are identical to the corresponding amino acid sequences depicted in SEQ ID NO 5, SEQ ID NO 6, SEQ ID NO 7, SEQ ID NO 8, SEQ ID NO 9 and SEQ ID NO 10, thereby preferably retaining the ability to neutralise inhibitory FVIII antibodies.

The present invention also relates to modified versions of the anti-idiotypic antibodies of the present inventions and also relates to F(Ab')2 fragments, Fab' fragments, Fab fragments and other fragments comprising at least one CDR region of an anti-idiotypic antibody directed against an antibody against the C2 domain of FVIII. The invention also relates to modified versions of said fragments.

Another aspect of the present invention is an isolated and purified peptide having a sequence selected from SEQ ID NO:5, SEQ ID NO:6, SEQ ID NO:7, SEQ ID NO:8, SEQ ID NO:9 and SEQ ID NO:10, or being at least 70% identical in amino acid sequence to a peptide with an amino acid sequence selected of SEQ ID NO:5, SEQ ID NO:6, SEQ ID NO:7, SEQ ID NO:8, SEQ ID NO:9 and SEQ ID NO:10. The isolated and purified peptides optionally are synthetically synthesized peptides and have a degree of purity of at least 96%, more preferably at least 98%, and even more preferably at least 99% as determined according to conventional methods of measuring purity.

Yet another aspect of the present invention is a monoclonal cell line expressing an anti-idiotypic antibody such as the deposited monoclonal cell line 14C12 with Accession Number LMBP 5878CB.

Another aspect of the present invention is a pharmaceutical composition comprising anti-idiotypic antibodies against inhibitory antibodies against the C2 domain of Factor VIII and fragments, peptides of said anti-idiotypic antibody and modified versions thereof, such as disclosed in details herein above.

Another aspect of the present invention is the use of an anti-idiotypic antibody or fragments, peptides of said anti-idiotypic antibody and modified versions thereof as a medicine.

Another aspect of the present invention is the use of an anti-idiotypic antibody or fragments, peptides of said anti-idiotypic antibody and modified versions thereof for the manufacture of a medicament for the prevention or treatment of bleeding, more particularly of bleeding in a haemophilia patient with inhibitory antibody against the C2 domain of FVIII.

Another aspect of the present invention is the use of an anti-idiotypic antibody or fragments, peptides of said anti-idiotypic antibody and modified versions thereof for the manufacture of a medicament for inhibition of production of inhibitory antibodies. According to one embodiment of this aspect of the invention, anti-idiotypic antibodies directed against FVIII inhibitors are used for the induction of apoptosis of B cells carrying anti C2 inhibitory antibodies. Thus the anti-idiotypic antibodies and their fragments of the present invention are capable of suppressing both the effector function of inhibitors to the C2 domain of FVIII (neutralisation of the effect of soluble antibodies) and the production of such antibodies (interactions with cells carrying identical or similar idiotopes as B02C11).

The present invention also relates to a method of preventing or treating the bleeding in patient, optionally a haemophilia patient, having inhibitory antibodies against the C2 domain of FVIII, the method comprising the step of administering to the patient an anti-idiotypic antibody, fragments, peptides or modified versions thereof.

The method also relates to a method of inducing apoptosis of B cells carrying anti-C2 inhibitory antibodies in a haemophilia patient with inhibitory antibody against the C2 domain of FVIII or fragments, peptides of said anti-idiotypic antibody and modified versions thereof.

Another aspect of the invention relates to the use of the anti-idiotypic antibodies directed against FVIII inhibitors for the detection of FVIII antibodies in body fluids.

The present invention will now be described in more details with reference to the following figures.

Throughout the Description, reference is made to the following sequences represented in the sequence listing:
SEQ ID NO: 1: nucleotide sequence of the heavy chain variable region of Ab 14C12
SEQ ID NO: 2: amino acid sequence of the heavy chain variable region of Ab 14C12
SEQ ID NO: 3: nucleotide sequence of the light chain variable region of Ab 14C12
SEQ ID NO: 4: amino acid sequence of the light chain variable region of Ab 14C12
SEQ ID NO: 5: amino acid sequence of CDR1 (H1) of the heavy chain variable region of Ab 14C12
SEQ ID NO: 6: amino acid sequence of CDR2 (H2) of the heavy chain variable region of Ab 14C12
SEQ ID NO: 7: amino acid sequence of CDR3 (H3) of the heavy chain variable region of Ab 14C12
SEQ ID NO: 8: amino acid sequence of CDR1 (L1) of the light chain variable region of Ab 14C12
SEQ ID NO:9: amino acid sequence of CDR2 (L2) of the light chain variable region of Ab 14C12
SEQ ID NO:10: amino acid sequence of CDR3 (L3) of the light chain variable region of Ab 14C12

DEFINITIONS

Factor VIII abbreviated as FVIII refers to the glycosylated blood coagulation factor with a molecular weight of 330 kD and 2332 amino acids which undergoes proteolytic processing.

Light chain of FVIII refers the proteolytic processed part of FVIII containing the A3, C1 and C2 domain.

C2 domain refers to the region spanning residues 2173 to 2332 of FVIII.

Phospholipid (PL) binding site refers to a region in the C2 domain between amino acids 2302 and 2332.

Idiotope refers to a single antigenic determinant.

Idiotype refers to the collection of idiotopes within the variable region that confers on an immunoglobulin molecule an antigenic individuality and is characteristic of a given antibody in an individual.

An Idiotype is said to correspond to the Internal image of an epitope when it conformationally mimics an antigenic epitope.

The term "Antibody" ("Ab") as used herein refers to intact monoclonal or polyclonal antibody molecules as well as fragments thereof comprising:
a) either both heavy and light chains, (such as Fab, F(ab)$_2$, F(ab')$_2$) or single heavy or light chains (e.g. light chain dimers), optionally including their constant region (or parts thereof, or optionally minor modifications (such as allotypic variants) of that constant region;
b) parts, thereof, in particular the specificity-determining parts thereof, i.e. the variable regions of the antibodies
c) subparts thereof, in particular the hypervariable parts thereof, such as peptides made up of stretches of amino acids comprising at least one CDR, optionally with adjacent framework sequences, e.g. of up to about 10 amino acid sequences at one or both CDR.

Optionally, according to the present invention, antibodies are IgG antibodies, particularly IgG1. F(ab')2 refers to the antibody fragment obtainable after pepsin cleavage and is built up of both light chains and parts of the heavy chains disulfide linked via the hinge region. The Fab fragment is obtainable from the intact antibody or from the F(ab')2 by papain digestion of the hinge region and contains a one light chain and one part of the heavy chain. Fragments of antibodies can also be obtained by synthesis or by recombinant methods described in the art.

An "inhibitory antibody" or "FVIII inhibitor" (Ab1) as used herein refers to an antibody which inhibits the activity of FVIII. According to a particular embodiment of the present invention, an inhibitory antibody is an antibody directed against the C2 domain of FVIII. Inhibitory antibodies can be either alloantibodies against exogenous FVIII or autoantibodies. Inhibitory antibodies can be of human or animal origin. Optionally, an inhibitory antibody is a human inhibitory antibody against human Factor VIII.

Anti-idiotypic antibody in the present invention refers to a second generation antibody (Ab2), which can be polyclonal but is preferably monoclonal and directed towards the variable part of inhibitory antibodies (Ab1). The anti-idiotypic antibodies according to the present invention preferably have the ability to neutralise inhibitory antibodies and optionally Ab1 production . . . The anti-idiotypic antibody of the present invention can be of human origin. The anti-idiotypic antibody of the present invention is preferably monoclonal and optionally recombinant.

The "ability to neutralise inhibitory antibodies" refers to a property of an anti-idiotypic antibody of the present invention to block the inhibitory activity of FVIII inhibitors (Ab1). This is can be determined by assaying the FVIII activity in the presence of inhibitor and anti-idiotypic Ab in an assay such as the Factor VIII chromogen test as described in Jacquemin et al. (1998) *Blood* 92, 494-506. Complementarity determining regions (CDR) in the present invention refers to the hypervariable amino acid sequences within antibody variable regions which interact with the epitope on the antigen. In one embodiment of the present invention the CDR regions are the CDR1, CDR2 and CDR3 regions of the variable light (VL) and heavy (VH) chains respectively (L1, L2, L3 and H1, H2, H3 respectively) of an anti-idiotypic antibody directed against an anti C2 domain inhibitory antibody. A specific embodiment relates to the corresponding regions in the anti-idiotypic antibody 14C12.

"Humanized antibody" as used herein, refers to non-human antibody molecules in which amino acids have been replaced in the non-antigen binding regions in order to more closely resemble a human antibody.

A "Reshaped human antibody" or a "Human hybrid antibody" as used herein, refers to a human antibody in which amino acids in the antigen binding regions have been replaced with sequences in accordance with the present invention, e.g. CDR's, or other parts of variable regions which have been derived from the repertoire of human antibodies.

Sequence comparisons. Comparisons of protein or nucleotide sequences are designated in terms of sequence identity or sequence similarity. Where in accordance with the present invention comparisons are made between amino acid sequences of two VH regions or of two VL regions, or comparisons are made between two nucleotide sequences encoding CDR regions, the level of sequence identity or similarity between two sequences may include having at least 70%, preferably at least 80% more preferably at least 90%, even more preferably at least 95% and most preferably at least 99% sequence identity or similarity between two sequences.

Nucleotide or amino acid sequences which are "identical" means that when two sequences are aligned, the percent sequence identity, i.e. the number of positions with identical nucleotides or amino acids divided by the number of nucleotides or amino acids (when of different length, in the shorter) of the sequences, is higher than 70%, preferably at least 80%, even more preferably at least 90%, most preferably at least 95-99%, more specifically is 100%. The alignment of two nucleotide sequences is performed by the algorithm as described by Wilbur and Lipmann (1983, *Proc Natl Aced Sci USA* 80:726) using a window size of 20 nucleotides, a word length of 4 nucleotides, and a gap penalty of 4.

Two amino acids are considered as "similar" if they belong to one of the following groups GASTCP; VILM; YWF; DEQN; KHR. Thus, sequences which are similar means that when the two protein sequences are aligned the percent sequence similarity is i.e. the number of positions with identical or similar nucleotides or amino acids divided by the number of nucleotides or amino acids (when of different length, in the shorter) of the sequences, is higher than 70%, preferably at least 80%, even more preferably at least 90% and most preferably at least 95-99%, more specifically is 100%.

Nucleotide sequences are considered as "similar" if they encode the similar or identical amino acid sequences, (i.e. between two nucleotide sequences encoding identical proteins the variation is within the bounds of genetic code degeneracy). "modified" denotes any protein (or polypeptide) molecule in which a single or a number of amino-acids have been either substituted by any other amino-acid residue or deleted. Such amino-acid substitution or deletion can be located anywhere in the protein molecule. It also denotes protein molecules in which amino-acid residues have been substituted and/or deleted at more than a single location. In the latter case, any combination of substitution and deletion can be considered. It also refers to polymorphisms (i.e. the regular and simultaneous occurrence in a single interbreeding population of two or more alleles of a gene, where the frequency of the rarer alleles is greater, typically greater than 1%, than can be explained by recurrent mutation alone.)

DETAILED DESCRIPTION OF THE INVENTION

The present invention will be described with reference to certain embodiments and to certain figures but the present invention is not limited thereto but only by the claims.

The present invention relates to anti-idiotypic antibodies against human Factor VIII inhibitory antibodies. Inhibitory antibodies against FVIII are most commonly developed in hemophiliacs, where the incidence of developing an inhibitor is 15-20%. Particularly haemophiliacs who are heavily exposed to FVIII concentrates, such as young patients or patients with a genetic defect that results in the absence of synthesis and/or secretion of FVIII protein (congenital hemophilia), are at high risk of developing FVIII inhibitors. However, inhibitory antibodies also occur in patients in the setting of auto-immune disorders, malignancies (such as lymphoproliferative disorders, lymphomas and solid tumors), drug reactions (e.g. penicillin, chloramphenicol, phenyloin), during pregnancy and in the post-partum state. Exceptionally, the presence of inhibitory antibodies can be idiopathic (eg in elderly patients). However, usually, the presence of inhibitory antibodies is associated with symptoms such as easy bruising and uncontrolled bleeding. This is usually referred to as acquired hemophelia. Thus, the present invention relates to the treatment or prevention of any condition associated with or characterised by the presence of inhibitory antibodies. The presence of inhibitory antibodies in a patient can be determined by different methods including quantitation of anti-FVIII activity, ELISA for FVIII inhibitors and purification using chromatography and immunoadsorbtion (each of these methods described in Algiman et al. 1992, above).

The present invention relates to anti-idiotypic antibodies capable of neutralising the inhibitory effect of FVIII inhibitors. Inhibition of FVIII by inhibitory antibodies can occur for instance by reducing the rate at which FVIII is activated by either binding to a proteolytic cleavage site of FVIII or by inducing a 3D conformational change in FVIII that renders it less amenable to proteolysis. Inhibition can also occur when antibodies interfere with the binding of FVIII to FIX and FX. Simultaneously or alternatively, inhibitory antibodies can interfere with the binding of vWF and/or PL to FVIII.

A particular embodiment of the present invention relates to anti-idiotypic antibodies against human Factor VIII inhibitory antibodies directed against the C2 domain of FVIII. Particularly, the invention relates to anti-idiotypic antibodies capable of neutralising by at least 50% the inhibition of FVIII procoagulant activity of inhibitory antibodies directed against the C2 domain of FVIII. The inhibition of procoagulant activity can be measured by the Factor VIII chromogen test as described herein. According to a particular aspect of the present invention, the anti-idiotypic antibodies are directed against inhibitory antibodies such as monoclonal antibody B02C11 (IgG4kappa antibody derived from the natural repertoire of a patient with inhibitor; Jacquemin M G, et al., 1998, Blood 92: 496-506) or other antibodies with similar C2 binding properties. More particularly, the anti-idiotypic antibodies are directed against FVIII inhibitors of which the VH domains are encoded by the DP5 VH gene segment derived from the VH1 gene family. Such and other Inhibitory antibodies can be obtained from humans (i.e. from the serum of patients which have inhibitory antibodies) or can be obtained from mice, guinea pigs, horses, goats, non-human primates and other mammals by immunization with FVIII, or fragments thereof, more particularly with a fragment comprising the all or part of the C2 domain.

According to a particular embodiment the present invention relates to ant-idiotypic antibodies against human Factor VIII inhibitory antibodies directed against the C2 domain of FVIII capable of neutralising by at least 50% the inhibition of FVIII procoagulant activity of inhibitory antibodies directed against the C2 domain of FVI, but which do not inhibit interfere with the physiological activity of FVIII, more particularly the binding of FVIII to vWF or PL. Methods for identifying the influence of an anti-idiotypic antibody on the ability of FVIII to bind to vWF and/or PL are described herein. These can be used for the selection of anti-idiotypic antibodies which do not interact with the binding of FVIII to PL or vWF, according to the present invention.

Additional methods for furthering the development of anti-idiotypic antibodies not interfering with the binding of FVIII to PL or vWF include, but are not limited to, a) using as immunogen, in the development of anti-idiotypic antibodies, an inhibitory antibody which itself has been generated against a modified FVIII, not comprising the PL binding domain (Pratt et al., above) or regions important for the binding of vWF (Jacquemin et al., 2003, *J Thromb Haemost* 1:456-463); b) using as immunogen, an inhibitory antibody from which the idiotope(s) recognizing the PL binding site or regions important for the binding of vWF of FVIII have been removed c) analysis of the similarity between the antigen binding site of the anti-idiotypic antibody obtained and the C2 domain of FVIII and i) selection of anti-idiotypic antibodies based on the fact that the correspondence between the idiotype of the anti-idiotypic antibody and FVIII does not include the PL binding site or regions important for the binding of vWF to FVIII or ii) removal of those regions within the idiotype of the anti-idiotypic antibody which correspond to the PL binding site of C2 or to regions for the binding of vWF to FVIII. Following each of these selection procedures, care should of course be taken that the selected or modified anti-idiotypic antibodies retain their ability to neutralise inhibitory antibodies.

According to the present invention, the monoclonal anti-idiotypic antibodies can be either of human or animal origin. Accordingly, the monoclonal anti-idiotypic antibody can be obtained in different ways. Cells producing anti-idiotypic antibodies can be obtained from peripheral blood lymphocytes from (e.g. haemophilia) patients with anti-FVIII antibodies or from healthy individuals. These can be immortalized using standard techniques and can be selected based on the ability of the anti-idiotypic antibodies to neutralize inhibitory antibodies, and, optionally, on the absence of interaction of the anti-idiotypic antibody with the binding of FVIII to PL and vWF. Optionally, the monoclonal antibodies produced by each of these cell lines can be sequenced for the identification of relevant idiotypes and selection based thereon, as described above.

Alternatively, the monoclonal anti-idiotypic antibodies of the present invention can be produced by on purpose immunisation of animals, such as mice, by injecting human FVIII inhibitory antibodies (such as the inhibitory antibody BO2C11 directed against the C2 domain of FVIII) in mice and then fusing the spleen lymphocytes with a mouse myeloma cell line, followed by identifying and cloning the cell cultures producing anti-idiotypic antibodies directed against factor VIII inhibitory antibodies.

The present invention thus further provides cell lines producing monoclonal antibodies which are reactive against FVIII inhibitors, produced as described above. These cell lines can be immortalized cells of human origin, optionally can originate from the patient to be treated. Alternatively, the immortalized cells can be of animal origin (particularly rodent). A particular embodiment of the present invention is provided by the deposited cell line 14C12 Accession Number LMBP 5878CB producing the anti-idiotypic antibody 14C12.

Optionally, the monoclonal antibodies produced in animals can be humanized, for instance by associating the binding complementarity determining region (CDR) of the non-human monoclonal antibody with human framework regions in particular the constant C region of human gene-such as disclosed by Jones et al. in *Nature* (1986) 321: 522 or Riechmann in *Nature* (1988) 332:323.

Alternatively, the anti-idiotypic antibodies can be obtained from human or animal sera by affinity purification on anti-FVIII antibodies (which themselves can be identified by immunoadsorption over insolubilized FVIII (as demonstrated by Algiman 1994, above and Gilles 1994, above). Optionally, the C2 domain can be used for affinity purification, in order to promote selection of anti-C2 (inhibitory) antibodies.

A particular embodiment of the present invention is provided by the anti-idiotypic monoclonal antibody 14C12 and antibodies including antibody fragments derived therefrom. According to a particular embodiment, the present invention relates to an anti-idiotypic antibody comprising the sequence of at least one of the CDR regions of the VH as identified in SEQ ID NOs 5, 6 or 7 or modifications of the 14C12 antibody as described hereunder.

The present invention also provides fragments of any of the above anti-idiotypic antibodies against inhibitory antibodies directed against the C2 domain of FVIII, such fragments including Fab, Fab', F(ab') 2, CDR's, single variable domains as well as modified versions thereof and combinations of these fragments and modifications.

More particularly, the present invention provides fragments and modified versions of the anti-idiotypic antibodies of the present invention, in particular fragments comprising complementarity determining regions ("CDR's") of the monoclonal anti-iditioypic antibodies, obtained as described above, as well as modified versions thereof. For instance, the invention provides antigen-binding fragments Fab, Fab' and F(ab')2 generated by proteolytic digestion of the said monoclonal antibodies using methods well known in the art, such as described by Stanworth et al., Handbook of Experimental Immunology (1978), vol. 1 chapter 8 (Blackwell Scientific Publications). Such fragments or artificial sequences, which contain the antibody binding site, may or may not have lost a number of properties of the parent antibody, such as complement activation or capacity to bind to Fc gamma receptors, however without losing their ability to inhibit inhibitory antibodies against FVIII. The present invention also includes single chain fragment variables (scFv), single variable domain fragments of the antibodies and combination of these fragments and of the above mentioned fragments. Antibodies where the respective CDR sequences are different in one arm compared to the other arm of the antibody are also within the scope of the invention.

The present invention further provides reshaped monoclonal antibodies or human hybrid monoclonal antibodies against FVIII inhibitory antibodies directed against the C2 domain of FVIII. By human hybrid monoclonal antibodies it is meant a hybrid antibody constructed from a human antibody and from variable regions in accordance with the present invention. The present invention also provides soluble or membrane anchored single-chain variable parts of the above monoclonal antibodies. These can be obtained based on methods described in the art, an example of which is provided herewith. The DNA sequences of the variable parts of human heavy and light chains are amplified in separated reactions and cloned. A fifteen amino-acid linker sequence, for instance (Gly4 Ser) 3, is inserted between VH and VL by a two-step polymerase chain reaction (PCR), for instance according to Dieffenbach and Dveksler, "PCR Primer, a laboratory manual" (1995), Cold Spring Harbour Press, Plainview, N.Y., USA. The resulting fragment is then inserted into a suitable vector for expression of single chain fragment variable (scFv) as a soluble or phage-displayed polypeptide. This can be achieved by methods well known to those skilled in the art, such as described by Gilliland et al., 1996, *Tissue Antigens* 47: 1-20. The present invention also includes a ligand comprising peptides representative of hypervariable regions of a monoclonal antibody which can be obtained by synthesis using an applied biosystem synthesiser, for instance a polypeptide synthesiser such as model 9050 available from Milligen (USA) or a model from a related technology, which alone or in combination with other or similar hypervariable regions will exert properties similar to that of the parent antibody. Fragments and peptides can be generated by recombinant DNA technology. Peptides with a length up to about 100 amino acid sequences can be made by synthetic peptide synthesis such as BOC (tert butyloxycarbonyl) or FMOC (9-fluorenylmethoxycarbonyl) synthesis and other techniques known in the art.

Optionally the amino and carboxy groups can be chemically changed in order to increase the stability and lifetime of the peptide (e.g. formylation, acetylation). Alternatively the peptide can be covalently or non-covalently bound to a carrier.

According to the present invention, anti-idiotypic antibodies for use in the treatment of patients suffering from FVIII inhibitors are optimally obtained by the following procedure:

a) isolating human antibodies directed against FVIII from a patient suffering from FVIII inhibitors
b) selecting from the antibodies obtained under (a) an antibody inhibiting FVIII coagulant activity based on its binding to C2
c) immunizing an animal with the antibodies selected under (b) or the antigen-recognizing part thereof (preferably at least VH and/or VL)
d) optionally, cloning the antibodies produced in the animal under (c)
e) selecting an anti-idiotypic antibody based on 1) its ability to neutralize the inhibitory activity of FVIII inhibitors, 2) the fact that it does not interfere with binding of FVIII to vWF or PL.
f) optionally, obtaining a humanized version, or an antibody fragment of the anti-idiotypic antibody selected under (e).

The present invention further provides a pharmaceutical composition for the prevention or treatment of bleeding in a haemophilia patient having inhibitory antibodies against the C2 domain of FVIII in humans, comprising, as an active ingredient, the monoclonal anti-idiotypic antibody and fragments and modified versions such as disclosed hereinabove, in admixture with a pharmaceutically acceptable carrier. More preferably the said monoclonal antibody is a monoclonal antibody, or a fragment, modified version or a sequence with high percentage of sequence similarity thereof, obtainable from the cell line 14C12 deposited with the Belgian Co-ordinated Collections of Microorganisms Accession Number LMBP 5878CB. A sequence compared to with the said monoclonal antibody is preferably at least 70% identical, more preferably at least 80% identical and even more preferably at least 90% identical and most preferably at least 95-99% identical, and the sequence identity is preferably particularly in respect to the complementarity determining regions of the antibody. A ligand in accordance with the present invention may also include a synthetic polypeptide of equivalent potency. The pharmaceutical composition of the present invention should comprise a therapeutically effective amount of the said above ingredient, such as indicated hereinafter in respect to the method of treatment or prevention.

Suitable pharmaceutical carriers for use in the pharmaceutical compositions of the invention are described for instance in Remington's Pharmaceutical Sciences 16 ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody active ingredient in the composition.

Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the monoclonal antibody active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may require protective coatings. The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

The present invention also provides the use as a medicament of a monoclonal anti-idiotypic antibody against FVIII inhibitory antibodies directed against the C2 domain of FVIII. More preferably the medicament used in the present invention is a means for reducing and/or preventing and/or treating bleeding in a haemophilia patient with inhibitory antibody against the C2 domain of FVIII. The said ligand may be provided to a patient by any means well known in the art, e.g. intravenously, intraarterially, parenterally or by catheterization.

The present invention therefore provides a method of treatment and/or prevention for preventing and/or treating and/or reducing the bleeding in patient, more particularly in a haemophilia patient, having inhibitory antibody against the C2 domain of FVIII in a mammal, preferably a human, comprising administering to a mammal in need of such treatment or prevention or attenuation of coagulation a therapeutically effective amount of a ligand as disclosed hereinabove. Preferably the said ligand is a monoclonal antibody obtainable from cell line 14C12 or an antigen-binding fragment Fab, Fab' or F (ab') 2, or one or more peptides comprising a complementarity determining region (CDR), a soluble or membrane-anchored single-chain variable part (scFv), a single variable domain or a modified version or combination of any of these elements. Optionally said method of treatment is combined with the administration to the patient of FVIII.

A therapeutically effective amount as used herein means from about 1 microgram to about 10 milligrams per kilogram of body weight, more preferably from about 10 micrograms to about 1 milligram per kilogram of body weight, even more preferably from about 1 to about 10 milligram per kilogram of body weight of the mammal to be treated. It will be appreciated that, in view of the long half-life time of most IgG antibodies, the ligands of the present invention which are monoclonal antibodies of the said class will enjoy a periodicity of treatment which participates in the comfort of the patient.

Haemophilia A patients with inhibitor frequently produce antibodies towards the FVIII C2 domain. The ligands of the present invention such as the antibody produced by the cell line 14C12 are therefore useful for the treatment of such patients, either in emergency situations, as for instance before a surgical procedure, or as a longer term treatment in which Ab 14C12 can induce an apoptosis of B cells carrying the corresponding anti-C2 antibodies.

The ligands of the present invention, such as the anti-idiotypic antibody AB 14C12 of cell line 14C12, have the capacity to neutralise in a functional coagulation assay by at least 50%, preferably by at least 70%, more preferably by at least 80% and most preferably by at least 90%, the FVIII inhibitory properties of inhibitory antibodies against the C2 domain of FVIII.

The reader skilled in the art will understand that from the knowledge of the sequence of AB 14C12 and that of the crystal structure of BO2C11 Fab fragment in combination with the C2 domain, several variants of Ab 14C12 can be envisioned. Thus, point mutations can be introduced in the Ab 14C12 VH region to reinforce the internal image of C2, thereby reinforcing the inhibitory capacity of Ab 14C12 on C2 binding of BO2C11 and the like. Alternatively, the sequence can be altered in such a way as to increase the number of contact residues in between BO2C11 and Ab 14C12, with or without maintenance of the C2 internal image. A particular aspect of this approach is to derive a 14C12 mutant antibody which would contain contact residues recognising amino acids included in the framework regions of BO2C11. The latter belongs to the DP5 heavy chain subfamily gene segments (Jacquemin M G et al in (1998) *Blood* 92: 496-506) as other antibodies with similar C2 binding properties. Since the frequency of DP5 family members is very low in the human repertoire, neutralisation of the entire DP5 subfamily can be achieved using Ab 14C12, thereby neutralising all inhibitory antibodies of which the VH domains encoded by the DP5 VH gene segment derived from the Vh1 gene family (Jacquemin et al (1998) cited supra; Van den Brink et al in (2000) *Blood* 99, 2828-2834.

According to the general knowledge of one skilled in the art, various different synthetic peptides can be prepared from the antibody 14C12. One or more of them, which alone or in combination can be used to neutralise BO2C11-like antibodies in vivo. In a preferred embodiment these peptides are derived from complementarity determining regions (CDR) of the heavy chain of the Ab 14C12 and are represented by the peptides with amino acid sequence GYTFTSSVMHWL [SEQ ID NO:5], GYINPYNDGTKYNEKFTA [SEQ ID NO:6] and SGGLLRGYWYFDV [SEQ ID NO:7]. In another preferred embodiment these peptides are derived from complementarity determining regions (CDR) of the light chain of the Ab 14C12 and are represented by the peptides with amino acid sequence RASQDITNTLH [SEQ ID NO:8], YVSQSIS [SEQ ID NO:9] and QQSTSWPYT [SEQ ID NO:10]. Thus, in one embodiment, synthetic peptides derived from Ab 14C12 complementarity regions (CDR) are used to infuse patients with inhibitory antibodies against the C2 domain of FVIII prior to surgery. The peptides combine with inhibitory antibodies and neutralise their inhibitory capacities. In a yet alternative embodiment, a recombinant polypeptide is made by combining the sequence of different CDRs, with appropriate linker polypeptide sequences to maintain a suitable 3-D conformation. The polypeptide is administered in patients prior to an emergency procedure such as surgery.

An additional application of the anti-idiotypic antibodies of the present invention, such as Ab 14C12, is their use to inactivate the production of FVIII inhibitors by the immune system. For instance, the anti-idiotypic antibodies of the present invention can be used to induce apoptosis of B cells carrying anti-C2 antibodies. Such B cells, as memory cells or as some antibody producing cells, express a surface antibody equivalent to its secreted form. Cross-linking of idiotypes at the B cell surface transduces a signal leading to inhibition of proliferation or apoptosis of the cell.

A further application of the anti-idiotypic antibodies of the present invention is their use in the detection and/or purification of FVIII inhibitors. Immunological detection and purification methods which can be applied in the context of the present invention are extensively described in the art. The following Examples, not intended to limit the invention to specific embodiments described, may be understood in conjunction with the accompanying Figures, incorporated herein by reference, in which:

FIG. 1: Dose-dependent neutralisation of the FVIII inhibition by BO2C11, neutralised by Ab 14C12 in accordance with an embodiment of the present invention.

Figure 2A:
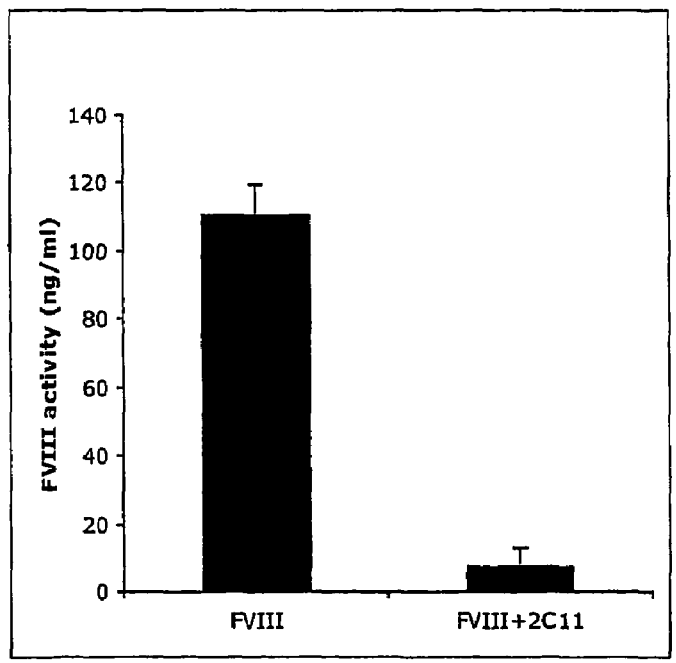
Figure 2B:
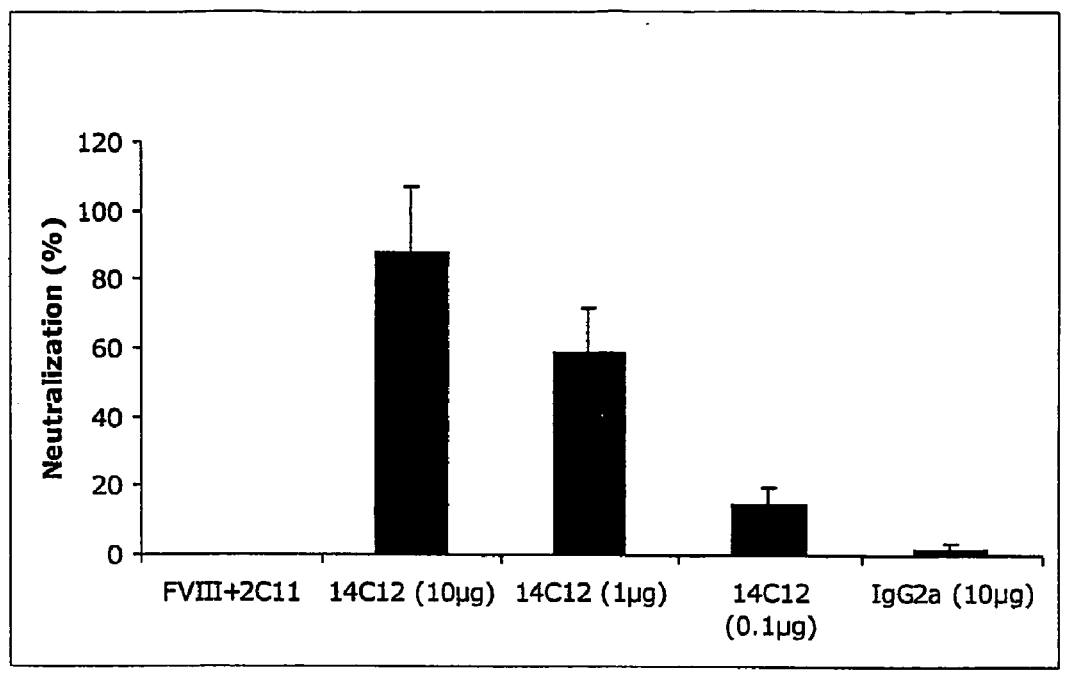
Figure 2C:
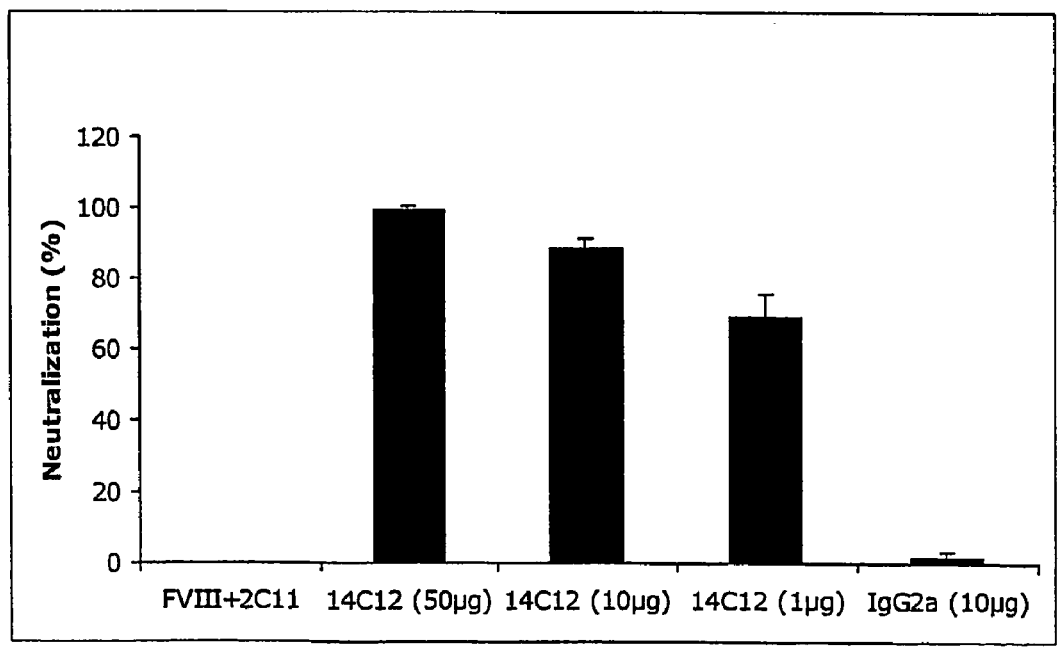

FIG. 2: Results of reconstitution experiments in FVIII−/− C57BI/6 mice in accordance with an embodiment of the present invention. Panel A displays the reconstitution with Factor VIII in the absence or presence of inhibitor Ab BO2C11; Panel B shows the dose dependent neutralisation by Ab 14C12 of BO2C11-mediated FVIII inhibition. Ab BO2C11 and Ab 14C12 were preincubated; in both Panel C and B, Ab14C12 administration was followed by BO2C11 and FVIII.

FIG. 3: Nucleotide and amino acid sequence of the heavy and light chain of anti-idiotypic antibody 14C12. The CDR regions are indicated under the amino acid sequence.

Figure 4:
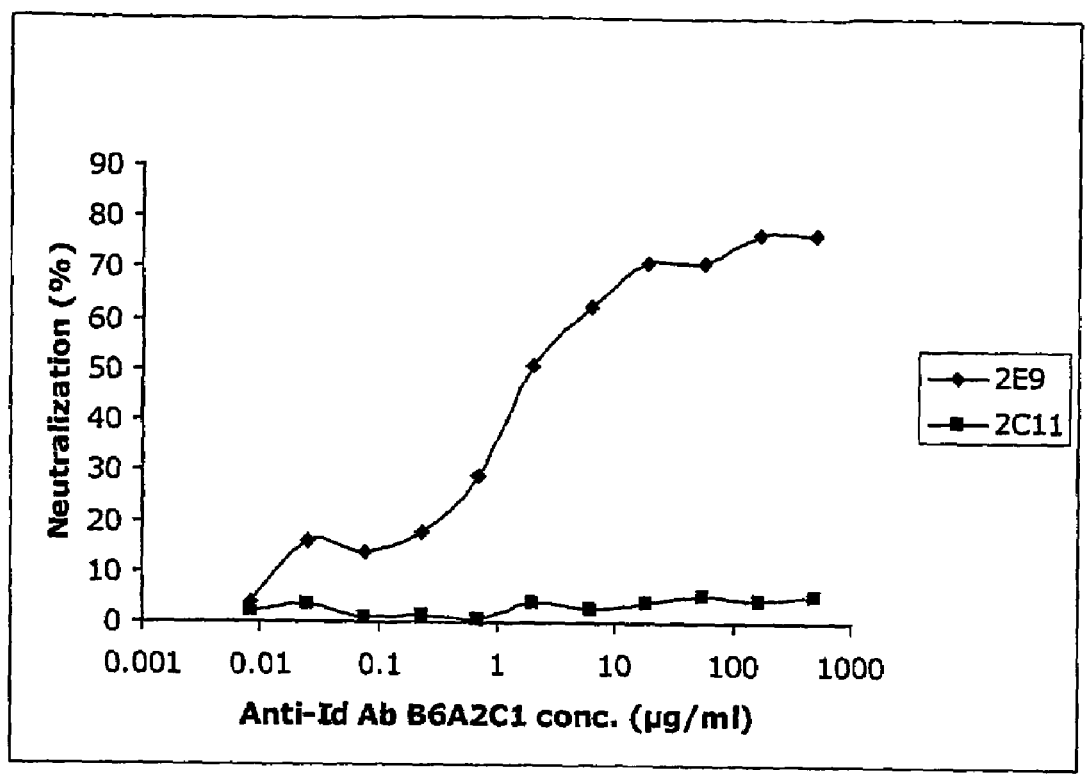

FIG. 4: Neutralisation of FVIII binding to human inhibitory antibodies against the C1 domain (2E9) and the C2 domain (BO2C11) by anti-idiotypic mouse MoAb against an inhibitor to the C1 domain (B6A2C1).

Figure 5:
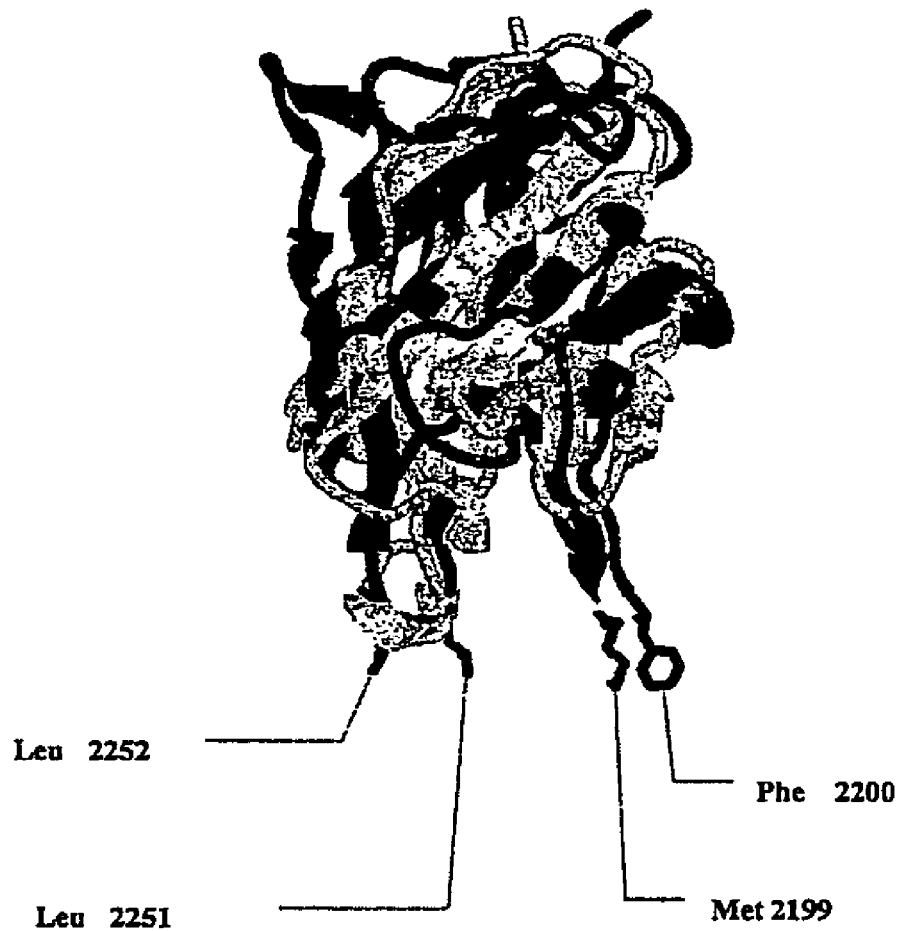

FIG. 5: Superposition of the C2 domain of FVIII (black) with Ab 14C12 VH region, wherein the dark grey lines represent the FVIII C2 domain, and the light grey lines represent the VH domain of 14C12.

Figure 6:
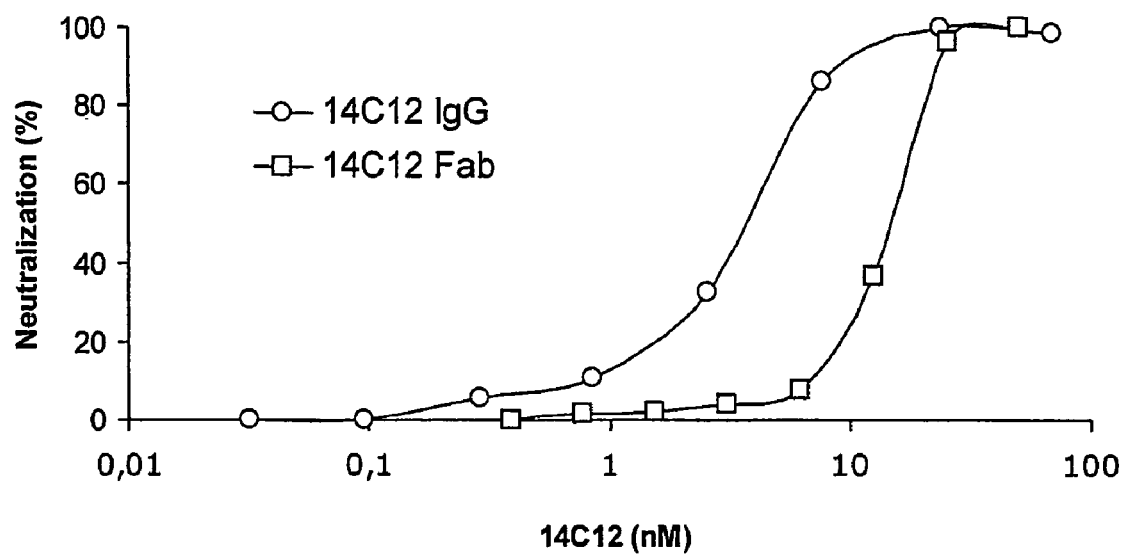

FIG. 6: Neutralization of the inhibitory activity of BO2C11 on FVIII upon addition of various concentrations of the anti-idiotypic antibody Ab 14C12. FVIII activity was measured in a functional chromogenic assay.

FIG. 7: Absence of inhibition of FVIII binding to phospholipids or VWF by Ab 14C12; FVIII was added to microtitration plates coated with either phosphatidylserine (panel A) or an antibody to VWF and purified VWF (panel B). The capacity of Ab 14C12 to inhibit the binding to either PL or VWF was assayed by adding increasing concentrations of Ab 14C12. Residual FVIII binding was evaluated using an antibody directed towards the heavy chain.

Figure 8:
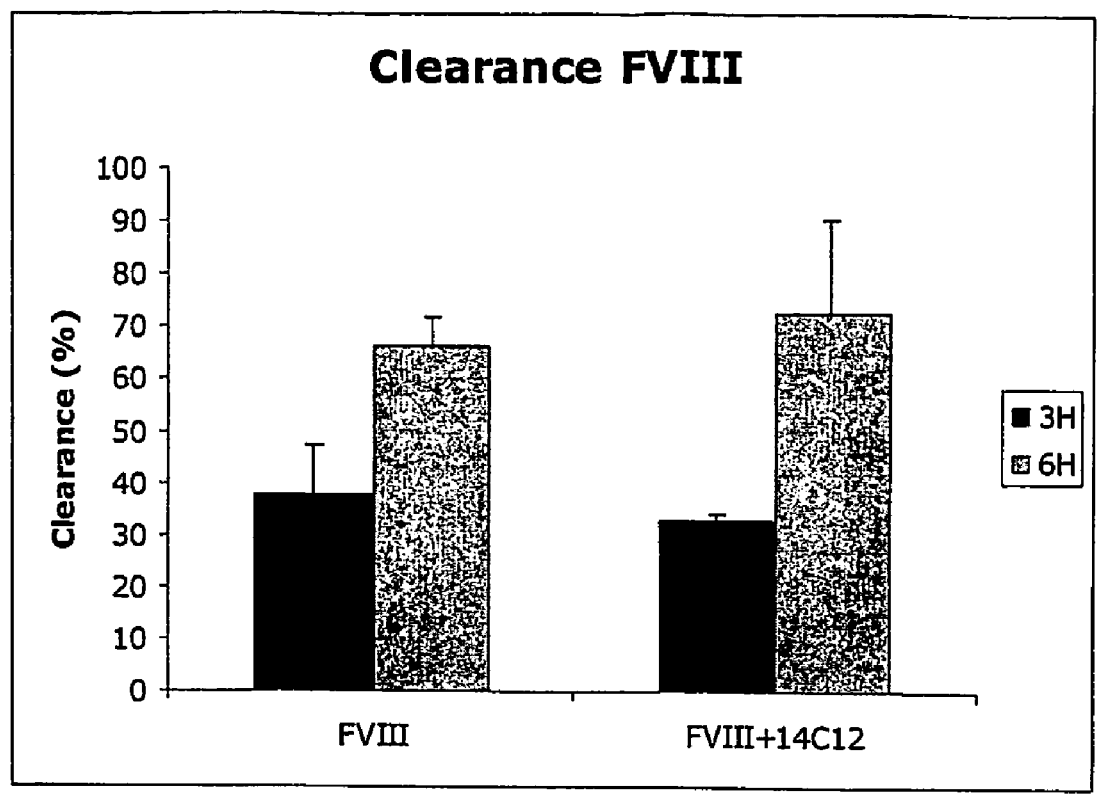

FIG. 8: Influence of Ab 14C12 on clearance of FVIIII from circulation; FVIII−/− C57BI/6 mice were injected IV with either FVIII alone (FVIII) or Ab 14C12 followed 15 minutes later by FVIII (VIII+14C12). The clearance rate of FVIII was evaluated by assessing FVIII function at 3 and 6 hours.

FIG. 9: Binding of Ab 14C12 to B-cells producing BO2C11. The BO2C11 lymphoblastoid cell line carrying surface antibody was incubated with Ab 14C12 (upper panel) or with a sham antibody of the same subclass (lower panel). The right shift of the curve shown in the upper panel indicates that 68% of the lymphoblastoid cell line BO2C11 is recognized by Ab 14C12.

EXAMPLES

Example 1

Generation of a Monoclonal Ab Against FVIII Inhibitor BO2C11

The Factor VIII specific human Ig4kappa BO2C11 antibody was used as for the generation of anti-idiotypic antibodies in mice. The properties of BO2C11 are described in Jacquemin et al (1998) *Blood* 92, 496-506. The nucleotide and amino acid sequences of the variable light and heavy chain of BO2C11 are disclosed in PCT patent application WO01/04269.

Balb/c mice were immunised in the footpad with BO2C11 emulsified in first complete and then incomplete Freund's adjuvant. After 4 such injections, mouse serums were tested in an ELISA system for the presence of antibodies recognising BO2C11, but not other anti-FVIII antibodies or unrelated antibodies of the same isotype. Splenocytes from mice producing specific anti-BO2C11 antibodies were fused with a myeloma cell lines to produce B cell clones (Kohler G et al. in (1978). *Eur J Immunol* 8:82-88.). These were expanded in culture and tested for BO2C11 specificity. One clone, 14C12, effectively bound to polystyrene plates coated with BO2C11.

The cell line 14C12 was deposited on Jul. 30, 2002 at the Belgian Coordinated Collections of Microorganisms (BCCM), LMBP (plasmid collection, Laboratorium voor Moleculaire Biologie, Universiteit, K. L. Ledeganckstraat 35, 9000 Gent, Belgium) with Accession Number LMBP 5878CB.

Example 2

In Vitro Properties of the Anti-idiotypic Antibody Obtained from Cell Line 14C12

The properties of the anti-idiotypic antibody (Ab 14C12) obtained from 14C12 cell line were examined in in vitro assay systems. Ab 14C12 was shown to bind to BO2C11 and to inhibit in a dose-dependent manner the binding of BO2C11 to its target antigen, the FVIII C2 domain. Moreover, the capacity of Ab 14C12 to neutralise the FVIII inhibitory properties of BO2C11 in a functional coagulation assay was also assessed. The chromogenic (Faktor VIII chromogen test, Dade Behring, Marburg, Germany) is based on the conversion of a colourless substrate, which is specifically cleaved by thrombin. The test system contains every reagent required to produce thrombin, except FVIII. The intensity of colour development over time is therefore proportional to the amount of FVIII added to the system. Addition of BO2C11 (0.1 μg/ml) completely inhibits the FVIII-dependent conversion (0.3 IU/ml) of the substrate.BO2C11 was added to the chromogenic assay at a final concentration of 0.1 μg/ml, which was determined as the minimum concentration of BO2C11 able to inhibit 100% of FVIII (0.3 IU/ml) in the test system. Different concentrations of Ab 14C12 were preincubated with this fixed amount of BO2C11 before addition of FVIII. The mixture was then applied to the chromogenic assay.

FIG. 1 shows that addition of Ab 14C12 to the test system neutralises in a dose-dependent manner the inhibitory capacity of BO2C11. Moreover, 50% neutralisation is obtained at a 1/1 molar ratio with BO2C11.

The capacity of Ab 14C12 to neutralise polyclonal anti-FVIII antibodies was tested in a chromogenic assay as described above. To this end, polyclonal antibodies of the patient from whom BO2C11 was derived were added to the system as a substitute for BO2C11. Under such conditions, up to 60% neutralisation was obtained upon addition of serial dilutions of Ab 14C12. It is known that such a polyclonal antibody preparation contains a significant amount of antibodies directed towards the heavy chain of FVIII, i.e. towards epitopes fully distinct from the C2 domain. It was therefore concluded that the 60% neutralisation of inhibition observed with polyclonal antibodies is an underestimation of Ab 14C12 capacity to neutralise anti-C2 inhibitor.

In addition, Ab 14C12 significantly neutralised the inhibitory properties of polyclonal antibodies from unrelated patients. Thus, polyclonal antibodies were added at different dilutions to an immunoprecipitation assay in which radiolabelled FVIII domains are produced by combined transcription/translation using rabbit reticulocytes (Promega kit, TNT couplet reticulocyte lynate, Madison, USA). The trace amount of radiolabelled domains produced is mixed with antibody samples and protein A Sepharose. Sepharose beads are added at a concentration at which essentially all antibodies are captured. After centrifugation and washing, the radioactivity is counted on the samples, which is proportional to the presence of antibodies with specificity for the FVIII fragment tested. Thus, polyclonal antibodies of 6 unrelated patients with haemophilia A and inhibitor towards the C2 domain were added at defined concentration in an assay in which the C2 domain was translated. Ab 14C12 was then added, at increased concentration, to all samples. Three out of the 6 samples yielded significant neutralisation (circa 50%) of the inhibitory properties of polyclonal antibodies, showing that Ab 14C12 recognises an epitope commonly expressed on human anti-C2 antibodies.

Example 3

In Vivo Properties of Ab 14C12

The capacity of Ab 14C12 to neutralise the FVIII inhibitory property of BO2C11 in vivo was examined in FVIII−/− C57BI/6 mice reconstituted with human recombinant FVIII (Singh I et al. in (2002) *Blood* 99: 3235-3240).

Such mice are considered to be a suitable animal model for haemophilia A, insofar as no FVIII activity or antigen can be detected, with an otherwise normal phenotype (Reipert B M et al. in *Thromb Haemost* 2000; 84: 826-32). Administration of 1 IU human FVIII in the tail vein of FVIII−/− C57BI/6 mice resulted in a plasma concentration of 110 ng/ml after 10 min, namely ±60% of the normal FVIII concentration in human plasma (1 IU or 192 ng/ml). When such mice are first injected with 0.5 μg of BO2C11, FVIII procoagulant activity is inhibited by 98%. The model was then used to determine whether Ab 14C12 had the capacity to neutralise the BO2C11-dependent inhibition of FVIII. Thus, different concentrations of Ab 14C12 were either mixed with a fixed amount of BO2C11 (0.5 μg) before injection of the complex in FVIII−/− mice, or directly infused in mice, followed by 0.5 μg of BO2C11 and 1 IU FVIII.

Pre-administration of 0.5 μg BO2C11 inhibited 98% of the FVIII procoagulant activity (FIG. 2 A). The fixed amount of BO2C11 was preincubated with various concentrations of Ab 14C12 (0.1 to 10 μg) and the mixture infused in FVIII−/− mice. A dose-dependent neutralization of BO2C11-mediated mediated FVIII inhibition was observed (FIG. 2B). The experiment was repeated but with sequential administration of Ab 14C12 followed by BO2C11 and FVIII, yielding an identical dose-dependent 14C12 mediated neutralisation (FIG. 2C).

It can be seen from FIGS. 2A, 2B and 2C that Ab 14C12 neutralises in a dose-dependent manner the inhibition properties of BO2C11, confirming thereby the potential of Ab 14C12 as a therapy for haemophilia A patients with inhibitor towards the C2 domain of FVIII. Interestingly, as shown in in vitro assays, 50% neutralisation was obtained at an equimolar ratio between BO2C11 and Ab 14C12. An Ab 14C12 molar excess of 3.5 was sufficient to fully neutralise BO2C11 and restoring a normal FVIII procoagulant activity.

Example 4

Binding Characteristic of Ab 14C12 to BO2C11

A thorough biochemical evaluation of Ab 14C12 was carried out. Ab 14C12 binds with high affinity to BO2C11, with $k_{on}$ and $k_{off}$ values of $10^5$ $m^{-1}$ $S^{-1}$, $10^{-5}$ $S^{-1}$ respectively, as measured using a surface plasmon resonance system. The VH and VL domains of Ab 14C12 were sequenced by conventional methods (FIG. 3). Thus Ab 14C12 belongs to the IJHV1 heavy chain antibody family, with a kappa light chain. The capacity of Ab 14C12 to inhibit the binding of BO2C11 to the FVIII C2 domain prompted the inventors to compare the sequence of the VH and VL domains of AB14C12 with that of C2. The CDR1 and CDR2 of VH contain 6 and 7 amino acid residues that are identical or homologous to the C2 domain, respectively. CDR2 is almost identical to the V2223-T2237 C2 region, which contains a crucial phospholipid-binding site and a number of contact residues for BO2C11. In addition, based on the sequence of BO2C11 variable parts (Jacquemin M G et al. in (1998) *Blood* 92: 496-506) and its crystal structure in association with C2 (Spiegel P. C. Jr. et al. in (2001) *Blood* 98: 13-19), putative contact residues between BO2C11 and Ab 14C12 were identified, some of which are located within the framework of BO2C11 variable parts. Taken together, these data show that the variable part of the heavy chain of Ab 14C12 contains both an internal image of C2 made of 13 identical or homologous amino acid residues, and a number of contact residues for the variable part of BO2C11.

Ab 14C12 therefore represents the first example of an anti-idiotypic antibody directed towards the C2 domain of FVIII, administration of which restores FVIII activity in vivo in a murine model of haemophilia A. As such, it discloses an effective therapy for haemophilia A patients with FVIII inhibitors.

To determine whether another anti-idiotypic antibody against an anti-FVIII C1 domain inhibitor, named B6A2C1 (Gilles J G et al in (1999) *Blood* 94, abstract 2048, 460a), can interfere with the binding of BO2C11 to FVIII, serial dilutions of this antibody were made and tested for their capacity to inhibit the binding of BO2C11 to FVIII-coated polystyrene plates. FIG. 4 shows that no inhibition occurred, indicating that B6A2C1 expressed no specificity for BO2C11.

Example 5

Analysis of the Homology between Ab14C12 and the FVIII C2 Domain

The in vitro and in vivo properties of the anti-idiotypic antibody (Ab 14C12) described in examples 2 and 3, respectively (see above), suggested that an extensive homology exists between the variable parts of the anti-idiotypic antibody and the C2 domain of FVII. The crystal structure of the C2 domain has been obtained (Pratt K et al. in (1999) *Nature* 402: 439-442). The sequences of the variable parts of the heavy and light chain of Ab 14C12 were therefore aligned to those of the C2 domain.

A significant homology was found with the VH region. Table 1 shows that 31 aminoacid residues were found either identical or similar. This included 13 residues associated with CDR regions, but clustering to the CDR1 (H1-16 residues) and CDR3 (H3-6 residues). Interestingly, a significant contribution is observed from residues located in framework regions (18 aminoacids). Moreover, only two residues (marked with an asterisk) of the VH region are mutated from the germine sequence of Ab14C12. All 31 residues are surface-exposed on C2, according to the crystal structure of the C2 domain (Pratt K et al. in (1999) *Nature* 402: 439-442), as well as on Ab14C12 VH region. A salient feature of this alignment is that it indicates the involvement of one of the two C2 phospholipid binding sites made up of Leu2251 and Leu2252 (total surface of 180 A), which correspond to Leu102 and Leu103 in Ab14C12 VH CDR3, while the second site (Met2199 and Phe2200) is not represented. Taken together these observations indicate that the VH region of Ab14C12 in its germine configuration carries an extended homology to the C2 domain. FIG. 5 illustrates the superposition of the C2 domain with Ab 14C12 VH region.

Another important aspect of the information provided in Table 1 is that the aminoacid residues of Ab 14C12 VH that mimic surface residues of the C2 domain are not part of a continuous sequence, but rather spread over the entire VH (from residues S7 to S121). This finding is in keeping with the demonstration that inhibitors to the C2 domain of FVIII bind to conformational epitopes rather than to sequential ones (see for instance the crystal structure of BO2C11 and the C2 domain in Spiegel P et al. (2001) *Blood* 98: 13-19).

Example 6

Determination of the Interacting Regions between BO2C11 and Ab14C12

The specificity of an antibody for a given antigen is generally dependent on residues located in one or two of the complementarity-determining regions (CDRs), often located in the VH region. Binding occurs corresponding to the most favourable thermodynamic conditions (Manivel et al. (2000) Immunity 13:611-620). Upon subsequent exposure to antigen, the antibody response is said to mature, a process which involves the random introduction of mutations in VH and VL regions. This is followed by a selection based on avidity for antigen. Therefore, the binding avidity of fully mature antibodies (which are the ones that can be detected or isolated from the natural repertoire of patients' B cells, in the present case towards FVIII) is dependent on cooperative forces brought about by residues located throughout entire VH and VL regions.

To determine whether the interaction between BO2C11 and Ab14C12 depended on residues located on a small number of discrete regions within the VH region, or, to the contrary, depended on residues scattered over the entire VH and VL regions, a sequence alignment was carried out between the VH and VL regions of BO2C11 and VH and VL regions of Ab 14C12. The results shown in Table 2 indicate that a significant contribution to mutual interaction is brought about by residues spread over VH and VL regions of both antibodies. This data confirms that a preferred way to obtain anti-idiotypic antibodies for administration in patients with FVIII inhibitors is to use complete anti-FVIII antibodies.

Example 7

Neutralization of BO2C11 Inhibitory Activity by Fab Fragments of Ab 14C12

Fab fragments of Ab 14C12 were prepared by digestion with papain agarose beads (Pierce, Rockford, Ill.) and purified by passage over a protein-A Sepharose column, according to methods well known to those skilled in the art.

To evaluate the capacity of Ab 14C12 Fab fragments to restore FVIII function in the presence of the inhibitor BO2C11, we first determined the concentration of BO2C11 required to inhibit 80% of FVIII activity in a functional chromogenic assay (Faktor VIII chromogen test, Dade Behring, Marburg, Germany) using 1 IU/ml of recombinant FVIII, as described in Example 2 (see above). The amount of BO2C11 required to inhibit 80% of FVIII activity was mixed with an equal volume of various concentrations of Ab 14C12 Fab fragments. The mixture was incubated for 1 h at 37° C. before addition of recombinant FVIII. An aliquot of the mixture was retrieved after a further 1-h incubation at 37° C. and added to the chromogenic assay reagents. Control experiments included recombinant FVIII incubated alone or with an Ab of unrelated specificity. FIG. 6 shows that Fab fragments neutralize 50% of BO2C11 inhibitory activity at a ⅛ BO2C11/Ab 14C12Fab molar ratio.

Example 8

Influence of Ab 14C12 on Binding of FVIII to vWF and PL

The FVIII C2 domain contains the binding site for phospholipids (PL) and major binding sites for von Willebrand Factor (vWF). Binding to PL is essential for the physiological activity of FVIII, namely the formation of the tenase complex with FIX and FX. vWF acts as a chaperone protein, protecting FVIII from early degradation and clearance.

The capacity of Ab 14C12 to inhibit the binding of FVIII to either vWF or PL was investigated as follows. Microtitration plates were coated with an anti-vWF antibody followed by purified vWF as described elsewhere (Jacquemin M et al. (1998) *Blood* 95: 156-163). Dilutions of Ab 14C12 (from 100 to 0.3 µg/ml) were prepared and an aliquot of each dilution was added to plates coated with vWF, followed by addition of FVIII at a final concentration of 1 IU/ml. Plates were incubated for 2 hours at room temperature. The binding of FVIII to vWF-coated plates was detected by addition of 2 µg/ml of biotin-labeled mAb15 (an anti-FVIII antibody recognizing a distant site of FVIII located on the heavy chain), followed by avidin-peroxidase and a specific substrate. To assess FVIII binding on PL, plates were coated with phosphathidylserine diluted at 10 µg/ml in methanol and the assay carried out as for the vWF-coated plates.

No inhibition of FVIII binding (and therefore of the C2 domain) to either vWF or PL was observed (FIG. 7). A control experiment in which Ab 14C12 was replaced by BO2C11 showed complete inhibition of FVIII binding to both vWF- and PL-coated plates (data not shown; see FIG. 3 in Jacquemin M et al. (1998) *Blood* 95: 156-163). It is therefore concluded that the extensive homology between the C2 domain and Ab 14C12 VH is not sufficient to interfere in the binding of FVIII to PL and/or VWF. Administration of Ab 14C12, or of one of its derivatives, as a mode of therapy for patients having inhibitors to the C2 domain should therefore not result in undesirable inhibition of FVIII functional properties.

Example 9

Influence of Ab 14C12 on the Clearance of FVIII

The clearance of FVIII from the circulation is at least in part due to the binding of the C2 domain to the LRP receptor (Saenko et al. (1999) *J Biol Chem* 274: 37685-37692; Lenting et al. (1999) *J Biol Chem* 274: 23734-23739) and could therefore be reduced by Ab 14C12. This was examined in FVIII-/- C57BL/6 mice reconstituted by tail injection of 1 IU human recombinant FVIII. Previous calculations have shown that the average human FVIII $t_{1/2}$ in this model was of 165 min. To ensure that Ab 14C12 did not modify FVIII clearance, C57BL/6 FVIII-/- mice were injected with 10 µg/ml of Ab 14C12 or of an IgG2a monoclonal antibody of unrelated specificity, followed 15 min later by an IV injection of 1 IU of recombinant FVIII. Blood samples were collected by venipuncture after 3 and 6 hours. Residual FVIII activity was evaluated by using a functional chromogenic assay (Faktor VIII chromogen test, Dade Behring, Marburg, Germany). No significant difference in FVIII $t_{1/2}$ was observed in the presence of Ab 14C12, as shown in FIG. 8. Administration of Ab 14C12, or of one of its derivatives, as a mode of therapy for patients having inhibitors to the C2 domain should therefore not alter the physiological clearance of FVIII.

Example 10

Binding of Ab 14C12 to BO2C11-producing B-cell Line

Ab 14C12 can be used to target memory B cells and some B cell lines producing producing antibodies inhibiting FVIII function. Such B lymphocytes express at their surface an antibody molecule with variable regions identical to those of the secreted form of the antibody. The binding of Ab 14C12 to its target cells can be used to transduce a signal that would result in cell death, or apoptosis, thereby purging the immune system from cells producing anti-FVIII inhibitors in an exquisitely specific manner.

The BO2C11 producing B-cell line (Jacquemin M et al. (1998) *Blood* 95: 156-163) produces the BO2C11 soluble antibody and expresses the antibody variable parts on its surface. To determine whether Ab 14C12 could bind to cell the cell surface, the BO2C11 cell line was washed in a buffer containing 0.5% bovine serum albumin and 2 mM EDTA, centrifuged at 400 g during 5 min and resuspended in the same buffer at a concentration of $5 \times 10^5$ cells in 100 µl. Antibodies, either Ab 14C12 or a sham IgG2 a antibody are then added to the cell suspension, using two different concentrations, either 1 or 10 µg/ml. The mixtures are incubated for 20 minutes on ice, washed by centrifugation and resuspension in buffer as described above. An anti-mouse IgG antibody coupled to FITC is then added to each cell suspension at a final concentration of 1 µg/ml for a further incubation on ice for 20 minutes. Cell suspensions are finally washed by centrifugation and resuspension in buffer as above. The final suspension was made to obtain a cell concentration of $1 \times 10^5$ in 500 µl for counting in a fluorescence-activated cell sorter.

FIG. 9 shows that after incubation with Ab 14C12, the BO2C11 cell line was specifically labeled with Ab 14C12, with 68% of cells positive for the antibody, while a sham antibody of the same subclass did not show any reactivity.

Thus, Ab 14C12 can be used as a specific reagent to target cells producing antibodies identical or similar to BO2C11, thereby providing a method for induction of apoptosis in a highly specific context.

TABLE 1

|  | VH 14C12 |  | C2 domain |
|---|---|---|---|
| FW1 | S7 | = | S2175 |
|  | P9 | = | P2177 |
|  | V12 | ± | M2180 |
|  | P14 | ± | S2182 |
|  | A16 | = | A2184 |
| CDR1 | A24 | = | A2192 |
|  | S25 | = | S2193 |
|  | G26 | = | S2194 |
|  | Y27 | = | Y2195 |
|  | F29 | = | F2196 © |
|  | T30 | = | T2197 © |
| FW2 | W36 | = | W2203 |
|  | K40 | = | K2207 |
|  | Q43 | ± | L2210 |
|  | L45 | = | L2212 |
|  | W47 | = | G2214 |
| CDR2 | D56 | ± | V2223 © |
| FW3 | S77 | = | P2226 |
|  | M81 | ± | L2230 |
|  | *E82 | ± | Q2231 |
|  | L83 | ± | V2232 |
|  | T87 | = | T2237 |
|  | *A92 | ± | T2241 |
| CDR3 | G101 | ± | S2250 © |
|  | L102 | = | L2251 © |
|  | L103 | = | L2252 © |
|  | G105 | ± | S2254 |
|  | D110 | = | E2259 |
|  | V111 | = | V2293 |
| FW4 | V120 | ± | L2302 |
|  | S121 | ± | T2303 |

Table 1: Sequence alignment between Ab 14C12 VH and FVIII C2 domain: Identical and homologous residues are indicated by "=" and "±", respectively. mAb14C12 mutated VH residues are shown with an asterisk. Putative C2 residues in contact with mAb2C11 are indicated by ©. CDR: complementarity determining region; FW: framework;

TABLE 2

| HC 2C11 | HC 14C12 | HC 2C11 | LC 14C12 |
|---|---|---|---|
| FW | *S67 >> A16 | FW | FW |
|  |  | V18 >> | H41 |

TABLE 2-continued

|  |  |  |  |  |  |
|---|---|---|---|---|---|
| FW 3 | G66 > S17 | FW 1 1 | P14 >> R45 |
|  | Q65 > V18 |  | K13 >> L46 |
| CDR 2 | F64 > K19 |  | K12 >> L47 |
|  | *E63 >> *L20 |  |  |
|  | A61 >> C22 |  | LC 2C11 |
|  | 2*S55 >> T28 | CDR 3 | C89 >> T69 |
|  | E54 >> F29 | FW 2 | Y88 >> *V70 |
| FW 2 | *V48 >> H35 |  | D83 >> I75 |
|  | E46 >> *L37 |  | E80 > V78 |
|  |  |  | L79 > E79 |
|  | LC 2C11 |  | R78 > T80 |
| CDR 1 | © Y33 >> V120 | FW 4 | I76 >> D82 |
|  | © S32 > S121 |  | T70 >> C88 |
|  | S31 > S122 |  | S68 > Q90 |
|  | © S30 >> A123 | CH 1 | S66 >> T92 |
|  | *F29 >> K124 |  | G65 > S93 |
|  | S28 >> T125 |  | P60 >> W94 |
|  | S26 >> T126 | CDR 2 | © T57 > T97 |
|  | R24 >> P128 |  | *T54 >> G100 |
|  | C23 > S129 |  | S53 >> G101 |
|  |  |  | © Y50 > L104 |
|  |  |  | I49 > E105 |

Table 2: Sequence correspondence between mAb2C11 and mAb14C12. Strength of interaction is depicted as ">>" and ">", respectively. mAb14C12 mutated VH residues are shown with an asterisk. Putative C2 residues in contact with mAb2C11 are indicated by ©. CDR: complementarity determining region; FW: framework; CH1: heavy chain first constant domain.

The invention claimed is:

1. A monoclonal anti-idiotypic antibody capable of neutralising a human Factor VIII inhibitory antibody, the said inhibitory antibody being directed towards the C2 domain of Factor VIII, characterized by the fact that the complementary determining regions CDR1, CDR2, and CDR3 of the variable heavy chains of said anti-idiotypic antibody have amino acid sequences depicted in SEQ ID NO: 5, SEQ ID NO: 6, and SEQ ID NO: 7, respectively and the complementary determining regions CDR1, CDR2, and CDR3 of the variable light chains of said anti-idiotypic antibody have amino acid sequences depicted in SEQ ID NO: 8, SEQ ID NO: 9 and SEQ ID NO: 10, respectively.

2. The monoclonal anti-idiotypic antibody according to claim 1, wherein the variable heavy chain of the said anti-idiotypic antibody is encoded by the nucleotide sequence depicted in SEQ ID NO: 1 or a nucleotide sequence having at least 95% sequence identity to SEQ ID NO: 1 or wherein the variable light chain of the anti-idiotypic antibody is encoded by the nucleotide sequence depicted in SEQ ID NO: 3 or a nucleotide sequence having at least 95% sequence identity with SEQ ID NO: 3.

3. The monoclonal anti-idiotypic antibody according to claim 1, wherein the variable heavy chain of the said anti-idiotypic antibody is encoded by the nucleotide sequence depicted in SEQ ID NO: 1 or a nucleotide sequence having at least 70% sequence identity to SEQ ID NO: 1 and wherein the variable light chain of the anti-idiotypic antibody is encoded by the nucleotide sequence depicted in SEQ ID NO: 3 or a nucleotide sequence having at least 70% sequence identity with SEQ ID NO: 3.

4. A fragment of the monoclonal anti-idiotypic antibody according to claim 1, which is an F(Ab')$_2$ fragment, an Fab' fragment, an Fab fragment or a modified version of said F(Ab')$_2$, Fab' or Fab fragment.

5. A monoclonal anti-idiotypic antibody capable of neutralising a human Factor VIII inhibitory antibody, the said inhibitory antibody being directed towards the C2 domain of Factor VIII, which is the monoclonal antibody Ab14C12 produced by the cell line 14C12 deposited at Belgian Coordinated Collection of Micro-organisms (BCCM) with Accession Number LMBP 5878CB or an antibody fragment derived therefrom, wherein said antibody fragment is capable of neutralizing said inhibitory antibody.

6. A monoclonal cell line expressing a monoclonal anti-idiotypic antibody in accordance with claim 1.

7. A monoclonal cell line, expressing an anti-idiotypic antibody capable of neutralising a human Factor VIII inhibitory antibody, the said inhibitory antibody being directed towards the C2 domain of Factor VIII, which is the cell line 14C12 deposited at BCCM with Accession Number LMBP 5878CB.

8. A pharmaceutical composition comprising a monoclonal anti-idiotypic antibody according to claim 1, in admixture with at least one pharmaceutically acceptable carrier.

9. The monoclonal anti-idiotypic antibody according to claim 1, wherein said anti-idiotypic antibody a) neutralises the anti-coagulant activity of FVIII inhibitors for at least 50% and b) does not interact with the binding of FVIII to vWF and phospholipids.

10. An antigen-binding fragment of the anti-idiotypic monoclonal antibody according to claim 1, capable of neutralizing a human factor VIII inhibitory antibody.

11. A pharmaceutical composition comprising a monoclonal anti-idiotypic antibody according to claim 5, in admixture with at least one pharmaceutically acceptable carrier.

12. A pharmaceutical composition comprising a fragment of the monoclonal anti-idiotypic antibody according to claim 4, in admixture with at least one pharmaceutically acceptable carrier.

13. A pharmaceutical composition comprising an antigen-binding fragment of a monoclonal anti-idiotypic antibody according to claim 10, in admixture with at least one pharmaceutically acceptable carrier.

14. A monoclonal anti-idiotypic antibody according to claim 1 or 5, which is a humanized monoclonal anti-idiotypic antibody.

15. A monoclonal anti-idiotypic antibody capable of neutralising a human Factor VIII inhibitory antibody, the said inhibitory antibody being directed towards the C2 domain of Factor VIII, characterized by the fact that the heavy chain variable region of said anti-idiotypic antibody comprises the amino acid sequence depicted in SEQ ID NO: 2.

16. A monoclonal anti-idiotypic antibody capable of neutralising a human Factor VIII inhibitory antibody, the said inhibitory antibody being directed towards the C2 domain of Factor VIII, characterized by the fact that the light chain variable region of said anti-idiotypic antibody comprises the amino acid sequence depicted in SEQ ID NO: 4.

17. A method of treatment of uncontrolled bleeding in a patient, wherein said patient has FVIII inhibitory antibodies that bind the C2 domain of FVIII, said method comprising administering to said patient a therapeutically effective dose of the pharmaceutical composition according to claim 8.

18. A method for the detection or purification of inhibitory FVIII antibodies from a sample which comprises contacting the sample with the antibodies of claim 1.

19. A method of making the monoclonal anti-idiotypic antibody of claim 1, said method comprising expressing a nucleotide sequence encoding the amino acid sequence of SEQ ID NO:2 and a nucleotide sequence encoding the amino acid sequence of SEQ ID NO:4 in a cell.

20. The method of claim 19, wherein said cell is cell line 14C 12 deposited at the Belgian Coordinated Collections of Micro-organisms under Accession Number LMBP 5878CB.

* * * * *

UNITED STATES PATENT AND TRADEMARK OFFICE
CERTIFICATE OF CORRECTION

PATENT NO. : 7,582,296 B2  Page 1 of 1
APPLICATION NO. : 10/523444
DATED : September 1, 2009
INVENTOR(S) : Gilles et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 531 days.

Signed and Sealed this

Ninth Day of November, 2010

David J. Kappos
*Director of the United States Patent and Trademark Office*